United States Patent
Sadiq et al.

(10) Patent No.: US 11,123,100 B2
(45) Date of Patent: Sep. 21, 2021

(54) MEDICAL APPARATUS AND ITS VISUALISATION

(71) Applicant: University Court of the University of Dundee, Dundee (GB)

(72) Inventors: Muhammad Sadiq, Dundee (GB); Sandy Cochran, Dundee (GB); Zhihong Huang, Dundee (GB); George Corner, Dundee (GB); Graeme McLeod, Dundee (GB); Patrick Carena, Dundee (GB)

(73) Assignee: UNIVERSITY COURT OF THE UNIVERSITY OF DUNDEE, Dundee (GB)

( * ) Notice: Subject to any disclaimer, the term of this patent is extended or adjusted under 35 U.S.C. 154(b) by 1037 days.

(21) Appl. No.: 14/777,514

(22) PCT Filed: Mar. 11, 2014

(86) PCT No.: PCT/GB2014/050717
§ 371 (c)(1),
(2) Date: Sep. 15, 2015

(87) PCT Pub. No.: WO2014/140556
PCT Pub. Date: Sep. 18, 2014

(65) Prior Publication Data
US 2016/0242811 A1    Aug. 25, 2016

(30) Foreign Application Priority Data
Mar. 15, 2013 (GB) ..................... 1304798

(51) Int. Cl.
*A61B 17/34* (2006.01)
*A61B 17/32* (2006.01)
(Continued)

(52) U.S. Cl.
CPC ........ *A61B 17/3403* (2013.01); *A61B 8/0841* (2013.01); *A61B 8/463* (2013.01);
(Continued)

(58) Field of Classification Search
CPC .... A61M 2205/00; A61B 10/00; A61B 17/00; A61B 2017/00; A61B 2090/00;
(Continued)

(56) References Cited

U.S. PATENT DOCUMENTS 4,249,539 A    2/1981  Mezrich et al.
5,095,910 A *  3/1992  Powers ................ A61B 8/0833
                                                    600/461
(Continued)

FOREIGN PATENT DOCUMENTS

CN    102209568 A    10/2011
CN    202198632 U     4/2012
(Continued)

OTHER PUBLICATIONS

Podder, T. K., et al. "Effects of velocity modulation during surgical needle insertion." 2005 IEEE Engineering in Medicine and Biology 27th Annual Conference. IEEE, 2006. (Year: 2006).*
(Continued)

*Primary Examiner* — Sean D Mattson
(74) *Attorney, Agent, or Firm* — Wolter VanDyke Davis, PLLC; Eugene J. Molinelli; Cian O'Brien

(57) ABSTRACT

An ultrasonically actuated medical implement is used in improving medical interventions and in certain instances to the generation of image data, in particular data acquired during a medical intervention or procedure. The medical implement employs a piezoelectric element which causes reciprocation between first and second mass assemblies in order to ultrasonically actuate a probe member and improve the visibility of the probe member to imaging methods. The
(Continued)

invention also concerns the visibility of structures in target regions to be imaged and how this may be enhanced using the medical implement of the invention.

18 Claims, 18 Drawing Sheets

(51) Int. Cl.
| | |
|---|---|
| *A61B 8/08* | (2006.01) |
| *A61B 8/00* | (2006.01) |
| *A61B 10/02* | (2006.01) |
| *A61B 90/00* | (2016.01) |
| *A61B 17/00* | (2006.01) |

(52) U.S. Cl.
CPC ............ *A61B 8/488* (2013.01); *A61B 8/5207* (2013.01); *A61B 8/5246* (2013.01); *A61B 17/320068* (2013.01); *A61B 8/465* (2013.01); *A61B 10/0233* (2013.01); *A61B 2017/0011* (2013.01); *A61B 2017/3413* (2013.01); *A61B 2090/3929* (2016.02)

(58) Field of Classification Search
CPC ................. A61B 8/00; A61B 17/3403; A61B 17/320068; A61B 8/5207; A61B 8/463; A61B 8/488; A61B 8/5246; A61B 8/0841; A61B 8/465; A61B 2017/0011; A61B 2017/3413; A61B 2090/3929; A61B 10/0233
See application file for complete search history.

(56) References Cited

U.S. PATENT DOCUMENTS

| | | | | |
|---|---|---|---|---|
| 5,329,927 | A * | 7/1994 | Gardineer | A61B 8/0833 600/439 |
| 5,343,865 | A | 9/1994 | Gardineer et al. | |
| 5,438,891 | A * | 8/1995 | Batten | B25B 13/488 81/56 |
| 5,967,991 | A | 10/1999 | Gardineer et al. | |
| 6,520,916 | B1 * | 2/2003 | Brennen | A61B 8/0833 600/463 |
| 6,702,761 | B1 * | 3/2004 | Damadian | A61B 10/0233 600/567 |
| 9,833,216 | B2 | 12/2017 | Ohuchi et al. | |
| 2003/0065263 | A1 * | 4/2003 | Hare | A61B 17/22012 600/439 |
| 2005/0021065 | A1 * | 1/2005 | Yamada | A61B 17/32002 606/169 |
| 2007/0197954 | A1 * | 8/2007 | Keenan | A61B 8/0833 604/20 |
| 2008/0208231 | A1 * | 8/2008 | Ota | A61B 17/320068 606/169 |
| 2009/0118641 | A1 | 5/2009 | Van Dam et al. | |
| 2010/0004558 | A1 | 1/2010 | Frankhouser et al. | |
| 2010/0047734 | A1 | 2/2010 | Harris et al. | |
| 2010/0286528 | A1 * | 11/2010 | Davis | A61B 18/1477 600/461 |
| 2011/0201931 | A1 | 8/2011 | Palmeri et al. | |
| 2012/0116248 | A1 * | 5/2012 | McWeeney | A61B 10/0283 600/567 |
| 2012/0130414 | A1 * | 5/2012 | Birkill | A61B 8/0841 606/185 |
| 2012/0209303 | A1 * | 8/2012 | Frankhouser | A61B 90/06 606/169 |
| 2013/0158390 | A1 * | 6/2013 | Tan | A61B 8/0841 600/424 |

FOREIGN PATENT DOCUMENTS

| | | |
|---|---|---|
| DE | 19750335 A1 | 6/1999 |
| DE | 11 2009 002 215 T5 | 7/2011 |
| EP | 1623674 A1 | 2/2006 |
| EP | 2064991 A2 | 6/2009 |
| EP | 2215969 A1 | 8/2010 |
| GB | 2367895 A | 4/2000 |
| GB | 2367895 A | 4/2002 |
| JP | H04227239 | 8/1992 |
| JP | H10118072 A | 5/1998 |
| JP | H1133028 | 2/1999 |
| JP | 2001-340336 | 12/2001 |
| JP | 2005319173 | 11/2005 |
| JP | 2008228861 A | 10/2008 |
| JP | 2014/28128 A | 2/2014 |
| JP | 2014028128 B2 | 5/2014 |
| KR | 10-1143663 A | 5/2012 |
| WO | WO9525464 A1 | 9/1995 |
| WO | WO2007067323 A2 | 6/2007 |
| WO | 2010047734 A1 | 4/2010 |
| WO | WO2013190409 A2 | 12/2013 |
| WO | WO2014002963 A1 | 1/2014 |

OTHER PUBLICATIONS

NuVue Therapeutics Inc., "Enhanced Ultrasound Guided Visualization", accessed via Wayback Machine, Apr. 11, 2011, Publisher: NuVue Therapeutics Inc., Published in: http://web.archive.org/web/20110411075316/http://www.nuvuetherapeutics.com/technologies/enhancedultrasound.html, retrieved Aug. 29, 2013.
UKIPO, "Search Report for the corresponding GB application 1304798.0", dated Feb. 10, 2014, pp. 1-3.
UKIPO, "Search Report for the corresponding GB application 1304798.0", dated Aug. 30, 2013, pp. 1-5.
ISA/EP, International Search Report and Written Opinion for the corresponding PCT application GB2014/050717, dated Jul. 18, 2014.
Office Action on Chinese Patent Application No. 2015-562302, issued by the State Intellectual Property Office of the People's Republic of China, Dispatched Jan. 15, 2018.
Office Action for JP Patent Application No. 2018-229043, issued by European Patent Office dated Sep. 9, 2019, pp. 1-7.
ISA/EPO: Official Action, European Patent Application No. 14710371.7, dated May 27, 2020, 4 pages.

* cited by examiner

MEDICAL APPARATUS AND ITS VISUALISATION

FIELD OF THE INVENTION

The invention relates to improving medical interventions and in certain instances to the generation of image data, in particular data acquired during a medical intervention or procedure. The invention also concerns the visibility of structures in target regions to be imaged and how this may be enhanced.

BACKGROUND TO THE INVENTION

Medical images of a subject can include information which is difficult to interpret and the manner in which information is presented in medical images can be of critical importance.

Different types of medical images are sensitive to different features in a region which is imaged. For example, MRI or ultrasound imaging is sensitive to soft tissues, X-ray imaging to denser bony tissues and Doppler imaging methods are sensitive to motion. However it may not be possible to clearly visualise all of the important or relevant information in a single type of image. For example, it can be difficult to locate the precise position of an introduced structure, such as a needle or a medical device in images optimised to show the features of soft tissues.

Displaying different types of images side by side or overlaid may make the images difficult to read, particularly when viewing changing real-time images or may obscure important information and there is a need for methods and apparatus to improve visualisation of information in medical images.

SUMMARY OF THE INVENTION

According to a first aspect of the invention there is provided a method of generating composite image data of a target region, the method comprising;
receiving first data obtained from measurements taken of a target region which includes an introduced structure;
receiving second data comprising image data of the target region;
determining a location, or a representation of a location of the structure, based on the first data; and
generating composite image data of the target region from the second data and including a determined representation of the location of the structure or portion of the structure.

Thus, composite image data is generated from the second data, which includes additional data representing the location of the structure, or at least a part of the structure. This may be particularly advantageous if display of the first and second data together may not be possible or desirable. For example, display of the first and second image data together may not be possible or desirable if an image generated from first data would obscure some or all of an image generated from the second data (or vice versa), or if interpretation of one or other image may be more difficult due to contrast effects, image artefacts, noise or other extraneous information, for example.

The representation of the location of the structure may include any indication of the location of all or a part of the structure, for example, a silhouette, phantom, outline or rendering of all or a part of the structure, a cursor, a crosshair, a vertex, or an apex or a more than one of each of or a combination of these.

The first data may be first image data and thus the method may comprise receiving first image data of the target region and receiving second image data of the target region.

The first and second data may be received simultaneously or sequentially. The first and second data may be received in any order and determining a location of the structure may be conducted before, or after, receiving the second data.

The first data and/or second data may be medical data, or medical image data. The target region may be a region of a subject (such as a patient). The structure may be a medical device or implement. Thus, the method may provide for generating a composite image of a subject showing a calculated image representative of the position of a medical implement or device in the subject, which may not be otherwise clearly visible in an image related to the second data.

For example, the first data and/or second data may comprise sonographic data (such as ultrasound data, elastographic image data or acoustic radiation data) or optical image data (such as diffuse optical image data or Raman image data) or radiological image data (such as X-ray, CT or PET image data), or magnetic or electrical image data (such as electroencephalographic image data, magnetoelectroencephalographic image data or MRI image data).

At least one of, or in some embodiments both of, the first and second image data may comprise ultrasound image data. The first image data may comprise Doppler ultrasound data and the second image data may comprise B-mode ultrasound data. The first image data may comprise both Doppler and B-mode ultrasound data.

In alternative embodiments, the first and second data may be geological data, geological image data, atmospheric image data, or may be materials image data.

The first image data may be complimentary to the second image data. For example, the first image data may contain more information concerning the structure than the second image data, and the second image data may contain more information about the target region than the first image data.

The first image data and/or second data may be received together with additional image data, and the method may comprise extracting first and/or second image data from additional image data. For example, the first image data and second image data may be received together (e.g. as part of the same image) and the method may comprise extracting the first image data and/or the second image data therefrom.

The first/second image data may be extracted from additional image data by thresholding. For example, the method may comprise extraction of data having intensity/amplitude values above a threshold value, extraction of pixels or voxels having a greyscale or RBG value above a threshold value, or a greyscale or RGB value which deviates from a mean value by more than a threshold amount. Alternatively or in addition, the method may comprise extraction of data by edge analysis, or by any other suitable data extraction method.

For example, the first image data may be Doppler image data received together with B-mode ultrasound image data, for example in the form of an image comprising a Doppler ultrasound image and a B-mode ultrasound image, and the method may comprise extracting Doppler ultrasound image data from combined Doppler and B-mode ultrasound image data.

The method may comprise transforming first image data (or first image data together with additional image data), for example by executing a compression algorithm, conducting a transformation from RGB to greyscale format, converting from phase data to magnitude or power data, executing a blurring algorithm, or any other suitable transformations known to those skilled in the art.

The method may comprise selecting a range of first image data. For example, a data range may be selected which includes data having data values above a threshold value (which may be the same or different to a threshold value used for extraction), or a data range may be selected which includes data values having a mean, or median value above a threshold value, or a data range may be selected within which a predetermined proportion of data points have data values above a threshold value.

Selection, extraction and/or transformation may be conducted so as to reduce processing demands, and enable images to be generated more rapidly or with less processing power. Selection, extraction and/or transformation may be conducted so as to improve the accuracy or precision of the calculation of the calculated image, for example by reducing the amount of noise in the data from which the calculated image data is generated.

Determining a location of the structure based on the first data may comprise determining a distance from the first data. For example, a signal corresponding to a distance of a structure from a transceiver may be determined from A-mode ultrasound data.

The method may comprise generating calculated image data, and generating the composite image data of the target region from the second data and the calculated image data.

The calculated image data may be generated by fitting the first data (which may be selected, extracted and/or transformed first image data) to structural data. The structural data reflects characteristics of the structure (e.g. the size or shape of the structure, or the location of edges or corners of the structure) and may be fit to first data in order to determine a location of the structure.

For example, the structure may comprise one or more straight edges and the structural data may comprise a template or mask around one or more straight edges. The structural data may comprise a template or mask of or around a periphery, or a part of a periphery, of the structure.

Fitting may comprise determining a maximum correspondence between the first image data (which may have been selected, extracted and/or transformed) and the structural data.

The method may comprise conducting a transformation, or a plurality of transformations of the structural data, to determine a maximum correspondence. The method may comprise conducting a plurality of transformations of the structural data, and determining a correspondence between the structural data and/or some or all of the transformations of the structural data and the first image data, to determine a maximum correspondence.

The method may comprise matrix matching or pattern matching, to determine a maximum correspondence.

The (or each) transformation may be a rotational transformation, a positional transformation (i.e. so as to change the coordinate position of structural data) or a scale transformation of structural data (i.e. in relation to the coordinate system of the first image data).

The method may comprise conducting a rotational transformation of the structural data or a plurality of rotational transformations.

The calculated image may be generated based on a correlated variable analysis of the of the first image data (which may have been selected, extracted and/or transformed), such as a principal component analysis (PCA) or a multilinear PCA component analysis or a factor analysis.

The analysis may be based on a property of the structure, such as an edge, corner or dimension of the structure.

Thus, location information, concerning the location of the structure, may be obtained from fitting the structural data to the first data.

Location information may comprise orientation information. Orientation information may comprise an orientation or slope of an edge of the structure, or position information (such as the position of a vertex of the structure) or scale information (such as the relative position of vertices or edges of the structure).

Determining a location of the structure may comprise determining an end point, or more than one end point, of the first image data. An end point may correspond to a part of the structure, such as an edge, corner or end of the structure.

An end point may be determined by conducting a threshold or other suitable analysis on the first image data based on location information. In some embodiments, an end point may be determined by conducting a threshold analysis (for non-zero PRG or greyscale pixel/voxel values along) a pathway derived from a correlated variable analysis or a determination of a maximum correspondence.

The end point may be determined from all of the first image data, or on a selection of the first image data, for example on first image data which has been extracted, selected or transformed.

Selection, extraction and transformation, end point determination and fitting may be conducted in any sequence.

The method may comprise fitting structural data to first image data and subsequently determining an end point and/or extracting, and/or the method may comprise selecting, extracting and/or transforming first image data and subsequently fitting structural data thereto.

The method may comprise updating the composite image data (i.e. generating updated composite image data). The method may comprise generating video image data from a sequence of generated composite image data.

The first image data, the second image data, the calculated image data and/or the composite image data may be data from which an image may be generated, such as raw data in a format output from an imaging apparatus. The first image data, the second image data, the calculated image data and/or the composite image data may be images or data in an image file format (e.g. PNG, JPEG, GIF, TIFF, BMP, etc.) or video file format (e.g. MPEG, AVI, MP4, 3GP, etc.).

Thus, the method may comprise generating a composite image of the target region from the second data and including a representation of the location of the structure or portion of the structure. The representation may include, for example, a silhouette, phantom, outline or rendering of all or a part of the structure, a cursor, a crosshair, a vertex, or an apex or a more than one of each of or a combination of these.

The first image data, the second image data, the calculated image data and/or the composite image data may be 2D image data or 3D image data.

The method may comprise generating 2D image data from 3D image data, for example by tomography.

The method may comprise displaying a composite image (derived from the composite image data). The composite image may be displayed on a display screen.

The representation of the location of the structure may be displayed over all or only a part of the composite image. The representation may be displayed some or all of the time. For example, the representation may be displayed consequent to a user command, such as a keyboard input or movement of a cursor, or the representation may be intermittent.

The method may comprise displaying a sequence of updated composite images (e.g. a video), which may be in real time.

The method may comprise generating video image data from a sequence of generated composite image data. Thus, the method may provide for interactively observing and controlling the position of the structure in the target region.

The method may comprise acquiring first and second data. The method may comprise acquiring first and second medical image data of a subject.

Accordingly the invention extends to a method of imaging a target region, for example a target region of a subject, comprising; acquiring first data by taking measurements of a target region which includes an introduced structure; acquiring second data comprising image data of the target region; determining a location or representation of a location of the structure, based on the first data; and generating composite image data of the target region from the second data and including data relating to a determined representation of the location of the structure, or portion of the structure derived from the first data.

The first data may be first image data related to a first imaging technique and the second data may comprise second image data related to a second imaging technique. Alternatively, the first and second data may relate to the same imaging technique and may for example be obtained or obtainable by acquiring image data sequentially or using different settings.

The first and second data may be obtained or obtainable from the same or different imaging apparatus.

The first data and second data may be acquired simultaneously or nearly simultaneously, i.e. at the same time or a short time apart, such as a fraction of a second or a fraction of the time between successive frames of a video. Accordingly, the composite image data may comprise calculated image data representative of the location of the structure when the second data was acquired.

The method may comprise introducing the structure into the target region. The method may comprise introducing a medical implement or a medical device into a subject, such as a needle or a drill. Thus, the method may enable improved visualisation of the location of a structure introduced into the target region, in some embodiments in real time.

Accordingly, in a second aspect, there is provided a method of treatment or surgery comprising introducing a structure into a target region of a subject, acquiring first data by taking measurements of the target region; acquiring second data comprising image data of the target region; determining a location of the structure or a representation of the location of the structure, based on the first data; and generating composite image data of the target region from the second data and including data relating to a representation of the determined location of the structure or portion of the structure.

The method may comprise ultrasonically actuating the introduced structure. Ultrasonic actuation has been found to improve the visibility of the structure to imaging methods such as B-scan or Doppler ultrasound, thereby improving the accuracy or sensitivity of the determined location.

The method may comprise causing the introduced structure (such as the probe member of a medical implement, introduced into a subject) to reciprocate with an amplitude of less than around 100 µm, such as less than around 50 µm, or even 30 µm.

Reciprocation of the structure with a small amplitude, in comparison for example to ultrasonically actuated drills or scalpels, has been found to improve the accuracy of the determined location of the structure, in use with motion sensitive imaging methods such as Doppler ultrasound.

The method may comprise causing the introduced structure to reciprocate around and along an axis.

According to a third aspect of the invention there is provided apparatus for generating composite image data of a target region;
the apparatus comprising a processing resource operable to receive first data of a target region which includes an introduced structure, and to receive second data comprising image data of the target region; to determine a location of the structure or a representation of a location based on the first data; and to generate composite image data of the target region from the second data and including data representative of the determined location of the structure, or portion of the structure based on the first data.

The apparatus, or the processing resource in particular, may be configured to carry out the method of the first aspect or second aspect.

The apparatus may comprise a processor, or more than one processor together functioning as the processing resource.

The apparatus may comprise one or more data storage devices. The apparatus may comprise a data storage device configured to receive and store first and/or second data, structure data, calculated image data and/or composite image data.

The apparatus may be configured to output composite image data. The apparatus may be configured to output composite image data to a data storage device, or to output or transmit composite image data to another apparatus, such as a computer or across a network.

The apparatus may comprise an image display device, such as a display screen, and the processing resource may be configured to output composite image data to the image display device.

Apparatus may comprise software code executed or executable on the processing resource. The software may be stored as software code on a computer readable storage medium accessible to the processing resource. The apparatus may comprise a computer readable storage medium on which the software code is stored.

According to a further aspect of the invention, there is provided a computer program preferably on a computer readable medium, the program having code or instructions for use in implementing any of the methods and/or to be used in conjunction with the apparatus defined herein.

According to a further aspect of the invention, there is provided a computer based or implemented system adapted to implement any of the methods and/or to be use in conjunction with the apparatus described herein.

The apparatus, and the processing resource in particular, may be configured to receive data from one or more imaging devices (directly, or indirectly—for example across a network or from a data storage device on which data acquired by an imaging device is stored).

In some embodiment, the apparatus may comprise an imaging device. The imaging device may be adapted to acquire first and/or second imaging data, to be received by the processing resource.

The imaging device may be a medical imaging device. For example, the apparatus may comprise an ultrasound probe or other components of an ultrasound scanning system.

The apparatus may comprise a first imaging device (adapted to acquire first data) and a second imaging device (adapted to acquire second image data).

The apparatus may further comprise a structure for introduction into a target region. For example, the apparatus may comprise a drill or a needle or a tube. The structure may be, or form part of, a medical implement or a medical device, for insertion or implantation into a subject. The apparatus may for example comprise a needle, cannula, a biopsy tool, trocar or an instrument for use in an endoscopic procedure. The apparatus may be, or form part of, a system for guided imaging procedures.

The apparatus may comprise an oscillating medical device or implement. The medical device/implement may comprise an oscillating or reciprocating component. The medical device/implement may be electromechanically actuated.

The apparatus may comprise an ultrasonically actuated medical implement.

Imaging techniques such as diffusion MRI, laser Doppler flowmetry and Doppler ultrasonography are sensitive to motion and the motion of introduced medical devices or implements may be visible in images generated from such techniques. However, motion of introduced medical devices/implements may be associated with artefacts in motion-sensitive imaging or may induce motion of surrounding parts of the target region, which can also be seen by motion-sensitive imaging. For example, an oscillating needle or drill may be much more clearly visible in a Doppler ultrasound image of a subject than in a B-mode ultrasound image, but its precise location within the Doppler ultrasound image may be obscured by signals resulting from motion in surrounding tissues or image artefacts.

The method and apparatus of the present invention enables the location of an oscillating (or otherwise moving) medical device/implement to be more precisely or accurately determined by motion-sensitive imaging techniques. This may be critical in a clinical context.

According to a fourth aspect of the invention there is provided an ultrasonically actuated medical implement, comprising:
a first mass assembly and a second mass assembly;
a piezoelectric element operable to cause reciprocation between the first and second mass assemblies along a principal axis; and
a probe member fixedly coupled to the first mass assembly (and thus and moveable in relation to the second mass assembly).

The medical implement may comprise a body and the body may comprise the first and second mass assemblies and the piezoelectric element. The first mass assembly may be moveable in relation to the body along the principal axis.

The body may define a channel extending along the principal axis. The first and second mass assemblies may define at least a part of the channel extending along the principal axis.

The probe member may be received in the channel.

The medical implement may comprise a probe member for use in percutaneous procedures, such as a biopsy tool, a curette, a needle (e.g. a hypodermic needle), a drill, a cannula, a trocar, an endoscope, or an instrument for use in an endoscopic procedure. Thus, the probe member may for example be a biopsy tool, a curette, a needle (e.g. a hypodermic needle), a drill, a cannula, a trocar or other elongate probe.

A variety of sizes may be suitable for use in the present invention, but desirably, the invention relates to implements with a diameter of between approximately 0.5 mm-1.5 mm. The probe member may be echogenic, such as an echogenic needle for use in ultrasound imaged procedures.

In use, the probe member may be caused to vibrate, by actuation of the piezoelectric element, with a reciprocating motion along the principal axis. Vibration driven at ultrasonic frequencies (in the range of approximately 10 kHz and above) reduces penetration force required to introduce the probe member into a subject (e.g. to penetrate skin or membranes) and reduces accretion. It has also been found that an ultrasonically actuated probe member has increased visibility in certain types of medical imaging, such as ultrasound imaging or Doppler ultrasound imaging.

The medical implement may comprise a body.

The channel may extend along the length of the body.

The probe member may extend from the body at each end of the channel.

A probe member (e.g. a needle or cannula) having a greater length than the body may be fixedly coupled to the first mass assembly so as to extend beyond each end of the body. Connection to the probe member can therefore be established without the need to contact the body, or any part of the channel or bore (as the case may be), so reducing or eliminating the need to sterilize the body. This is of particular benefit for establishing a fluid connection between a tubular probe member, such as a needle or cannula.

The medical implement may comprise a bore extending along the principal axis and the probe member may be received in the bore. The body may have a throughbore extending along the principal axis.

Accordingly, the invention extends to an ultrasonically actuated medical implement, comprising:
a body having a first mass assembly and a second mass assembly, and a piezoelectric element operable to cause reciprocation along a principal axis between the first and second mass assemblies;
a channel extending along the principal axis; and
a probe member received in the channel and fixedly coupled to the first mass assembly and extending from the body at each end of the channel.

The medical implement may comprise a connection arrangement for coupling, and preferably releasably coupling, the probe member to the first mass assembly. The first mass assembly may comprise a connection arrangement.

The connection arrangement may comprise engagement members, moveable into engagement with the probe member, to thereby couple the probe member to the first mass assembly.

The probe member need not be specifically adapted for coupling with the connection means and the connection arrangement may enable standard a probe member, such as a disposable needle, cannula and the like, to be coupled to the first mass assembly. Additionally, the range of motion of engagement members may be sufficient to couple to probe members of various sizes, such that a single implement may be used with multiple types or sizes of probe members.

The invention therefore extends to an ultrasonically actuated medical implement, comprising:
a first mass assembly and a second mass assembly, defining a channel extending along a principal axis, and a piezoelectric element operable to cause reciprocation along the principal axis between the first and second mass assemblies;
a connection arrangement, comprising moveable engagement members, for fixedly coupling the probe member to the first mass assembly; and
a probe member received in the channel and fixedly coupled to the first mass assembly by the engagement members.

The probe member may be fixedly coupled to the first mass element by friction with the engagement members.

The engagement members may form an interference fit with the probe member.

The engagement members may be moveable radially into engagement with the probe member. In some embodiments, at least a portion of the probe member is generally cylindrical.

Radially moveable engagement members may be configured to apply clamping pressure evenly to a probe member, and thereby reduce the risk of damaging the probe member.

Radially moveable probe members may be evenly distributed around an axis.

The connection arrangement may comprise at least two, or at least three engagement members.

The engagement members may be configured to engage along a length of the probe member, so as to distribute clamping force.

The engagement members may be resiliently biased. The engagement members may be resiliently biased away from the channel.

The engagement members may be separate or may be formed from a single piece of material.

In some embodiments, the connection arrangement is configured to couple the probe member to the first mass assembly by way of a single manual operation. That is to say, the connection arrangement may be changed from a first configuration in which the probe can be introduced into and removed from the channel, to a second configuration in which the probe member is fixedly coupled to the first mass assembly, by a single manual operation.

A single manual operation, i.e. an operation possible by gripping the engagement members or the locking member and executing a single motion, may be performed quickly and reliably. This is of particular importance in a clinical setting. In addition, the likelihood of over tightening or under tightening is reduced.

Thus, the invention also extends to an ultrasonically actuated medical implement, comprising:
a first mass assembly and a second mass assembly, defining a channel extending along a principal axis;
and a piezoelectric element operable to cause reciprocation along the principal axis between the first and second mass assemblies;
a connection arrangement for fixedly coupling the probe member to the first mass assembly, and configured to couple the probe member to the first mass assembly by way of a single manual operation.

The connection arrangement may comprise a locking member, moveable in relation to the engagement members, to bring the engagement members into engagement with the probe member.

The connection arrangement may be configured to couple the probe member to the first mass assembly by moving the locking member in relation to the engagement members. The probe member may be coupled to the first mass assembly by moving the locking member in relation to the engagement members with a single manual operation.

The locking member may be rotatable in relation to the engagement members. Once engagement members loosely contact the probe member, rotation of the locking member by a part of a turn (for example half a turn or more preferably a quarter of a turn) is sufficient to place the connection arrangement in the second configuration. A rotatable locking or engagement member may be gripped (for example between a thumb and forefinger) and turned through a part of a turn to couple the probe member to the first mass assembly, without the need to release and again grip the member to complete the coupling. Thus, the probe member may be couple coupled by way of a quick and reliable single manual operation.

Alternatively, or in addition, the locking member may be slideable in relation to the engagement members, for example along (and/or around) the principal axis. For example, the locking member may comprise a tapered cup and the engagement members may be slideable along the principal axis in relation to the tapered cup.

The connection arrangement may comprise a chuck or a collet. A chuck or collet may be adapted to receive probe members having a range of external diameters.

The locking member may be threaded around a collet, or may be slideable in relation to a collet.

The locking member and engagement members may have opposed tapered faces.

Motion of the engagement members in relation to the locking member may be indexed. For example, locking or engagement members may comprise a cam, or a ridge, so that relative motion of the locking and engagement members is biases away from the cam or the ridge. Thus, in use, the locking member does not move smoothly in relation to the engagement members (between first and second configurations), and a user feels a change in resistance to movement when sufficient force has been applied to lock the probe member in place.

Relative motion of the engagement members and locking member may be torque limited, for example by way of a ball and detent clutch mechanism.

The medical implement may be configured to cause the probe member to reciprocate along the principal axis with an amplitude of less than around 100 μm, such as less than around 50 μm, or even 30 μm. In some embodiments, the probe member reciprocates along the principal axis with an amplitude of less than around 10 μm.

Ultrasonic actuation has previously been associated with delivering energy to a target region of a subject (e.g. ultrasound actuated scalpels or drills). The amplitude of motion is therefore normally optimised to deliver as much energy as possible and so probe members of known devices move with as large an amplitude as possible—in the range of hundreds of microns in some cases. However, such amplitudes have been found to produce artefacts in motion sensitive imaging methods such as B-scan or Doppler ultrasound. It has now been found that a smaller range of motion reduces the severity of imaging artefacts, whilst maintaining the visibility of the ultrasound actuated probe member in motion sensitive imaging. It has also been found that the location of a probe member, using the method of generating composite image data described above, may be determined more precisely or accurately when the probe member reciprocates with a smaller amplitude.

The amplitude of motion may be mechanically limited, for example by end stops which limit the range of motion of the first mass assembly. The amplitude of motion may be limited by the maximum deflection of the piezoelectric element. The amplitude of motion may be limited by the drive voltage applied to the piezoelectric element.

The invention therefore extends to an ultrasonically actuated medical implement, comprising:
a first mass assembly and a second mass assembly;
a probe member fixedly coupled to the first mass assembly and moveable in relation to the second mass assembly with an amplitude of less than 30 μm; and
a piezoelectric element operable to cause reciprocating motion along a principal axis between the first and second mass assemblies.

Actuation of the medical implement may cause the first and second mass assemblies to reciprocate along and around the principal axis.

For example, the piezoelectric element may comprise a motor operable to impart a rotational force between the mass assemblies, or the first mass assembly may be adapted to flex or compress, or a portion of the first mass assembly may run within a helical channel, so as to transfer axial force into rotational motion.

Reciprocation of the mass assemblies along and around the principal axis results in concomitant motion of the probe assembly along and around the principal axis, in use. It has been found that rotation of the probe member along and around the principal axis reduces accretion and also reduces the forces which must be applied in order to penetrate tissues of a subject. This is of particular importance for low amplitude reciprocation and in use of delicate probe members probe to bending.

The medical implement may comprise any suitable type of piezoelectric element capable of causing cause reciprocation along a principal axis between the first and second mass assemblies. For example, the piezoelectric element may comprise one or more rings, dics or bars. The medical implement may comprise a Langevin type transducer, or one or more polycrystalline or single crystal transducers, or may comprise binary or tertiary ceramic piezoelectric material, or organic or polymeric piezoelectric material. The piezoelectric element may comprise a flextensional transducer, such as a cymbal transducer.

The piezoelectric element may be coupled to the first and the second mass assembly. The piezoelectric element may be disposed between the first and the second mass assembly. The piezoelectric element may be disposed around a bore.

The first mass assembly typically has a smaller mass than the second mass assembly. The ratio of the first mass assembly to the second mass assembly may in the region of 1:5-20, such as 1:7.5-12.5, such as 1:10. The first mass assembly and the probe member may together have a lower mass than the second mass assembly. Thus, in use, a greater proportion of the ultrasonic energy is transferred by the piezoelectric element to the first mass assembly and probe member than to the second mass assembly.

The first and/or second mass assembly may comprise a collection of parts, or may be of unitary construction.

The first and/or second mass assembly may define at least a part of a bore.

The first and/or second mass assembly may be generally symmetrical around the channel (or bore, as the case may be) and may be formed generally as a ring.

The first mass assembly may comprise a connection arrangement for releasable coupling to the probe member. Thus, the probe member may be removed for cleaning or disposal after use.

In a fifth aspect of the invention there is provided a body of a medical implement, the body comprising:
a first mass assembly and a second mass assembly;
a piezoelectric element operable to cause reciprocation between the first and second mass assemblies along a principal axis; and
a connection arrangement for releasably and fixedly coupling the first mass assembly to a probe member.

The body may be connected to a probe member so as to form a medical implement according to the fourth aspect.

The medical implement may comprise or be connectable to drive circuitry, operable to apply a drive voltage to the piezoelectric element. For example, the medical implement may comprise or be connectable to a signal generator.

The amplitude and/or frequency of the drive voltage may be adjustable. Thus, the voltage or amplitude of the drive voltage may be adjusted according to the requirements of a particular procedure, type or size of probe member or mechanical properties of the target region.

The medical implement may form part of a medical system, comprising the medical implement, and imaging apparatus. The medical system may comprise apparatus for generating a composite image, according to the third aspect.

According to a sixth aspect of the invention, there is provided a method of treatment or surgery comprising introducing a probe member of an ultrasonically actuated medical implement of the fourth aspect, into a subject. The method may comprise acquiring an image of a target region of the subject, such as a B-mode ultrasound image. The method may comprise generating composite image data of the target region, by the method of the first or second aspect.

Further preferred and optional features of each aspect of the invention correspond to preferred and optional features of each other aspect of the invention.

The term "comprise" as used herein is to be interpreted as "consists solely of", or "includes, in addition to other features".

DESCRIPTION OF THE DRAWINGS

Embodiments are now described, by way of non-limiting example, and are illustrated in the following figures in which.

DETAILED DESCRIPTION OF AN EXAMPLE EMBODIMENT

Figure 1:
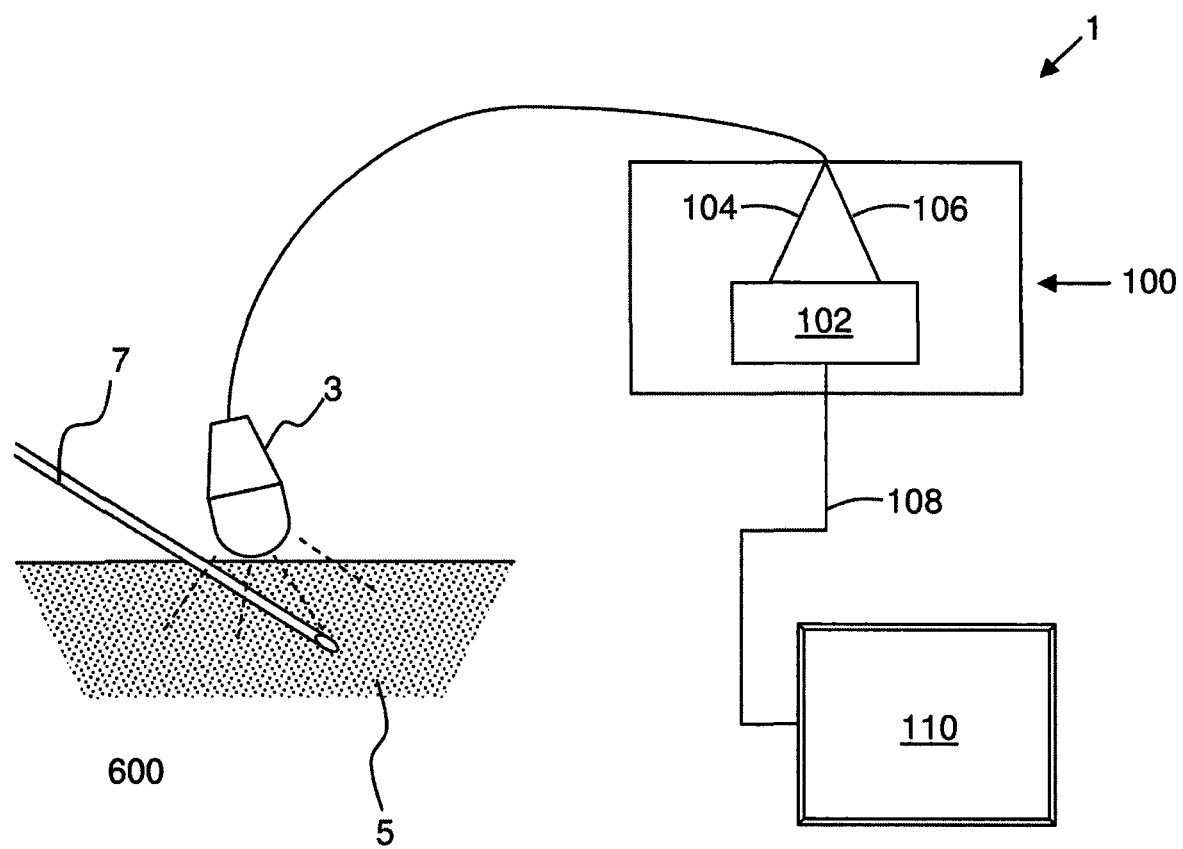
FIG. 1 is a schematic diagram of a medical imaging system.

FIG. 1 shows a medical imaging system 1 which includes apparatus 100 for generating composite image data, according to an embodiment of the present invention. The system 1 has an imaging device 3 connected to a processing resource 102. A target region 5 of a subject, such as a patient, includes an introduced structure 7 and the imaging device is operable to acquire image data of the target region.

The processing resource is operable to receive first data 104 and second data 106, which comprises image data of the target region, from the imaging device. The processing resource is operable to generate composite image data 108, which is output to a display device 110, as described in further detail with reference to FIG. 2.

In the example shown, the imaging device is configured to acquire Doppler ultrasound image data (first image data) and B-mode ultrasound image data, and the imaging device 3 is an ultrasound probe and the introduced structure is an ultrasonically vibrating needle (described in further detail below). The ultrasound probe is configured to acquire Doppler ultrasound image data (first data) and/or B-mode ultrasound image data (second image data) of a target region of a patient. The particular embodiment described should not be construed as limiting and the image data processing methods described below may also be applied to other forms of medical imaging and, accordingly, are suitable for use with other types of imaging systems or data acquired by other types of imaging techniques. Indeed, the method also has non-medical applications, for example in the fields of materials testing or surveying.

Figure 2:
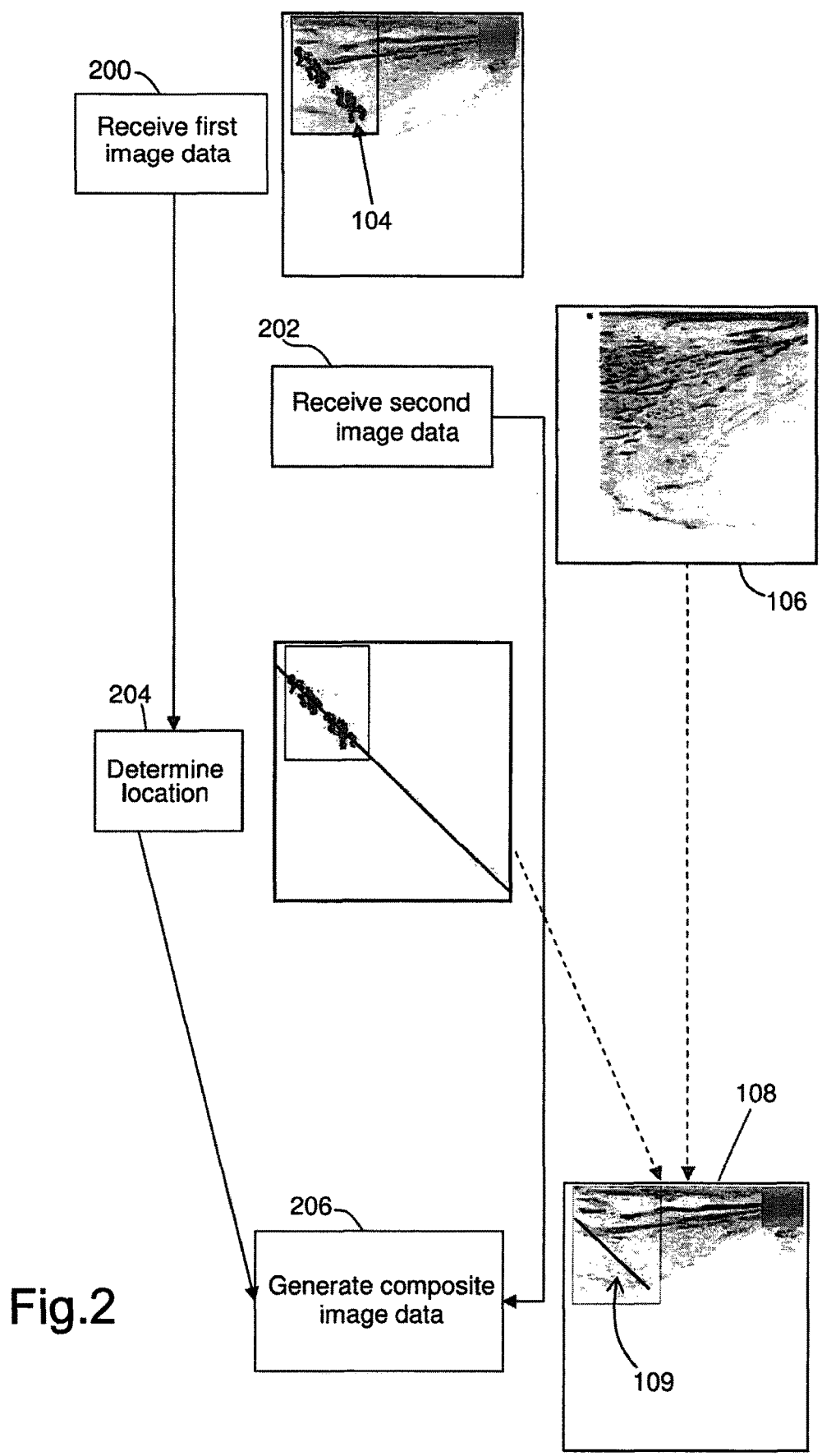
FIG. 2 is a flow diagram of a method of generating composite image data

Generation of a composite image will now be described with reference to FIG. 2. At stage 200, first image data 104 of the target region is received. At stage 202, second image data of the target region is received. At stage 204, a location of the introduced structure 7 is determined. At stage 206 composite image data is generated from the second image data and includes data 109 which is representative of the location of the structure 7, as determined at stage 204.

Figure 3:
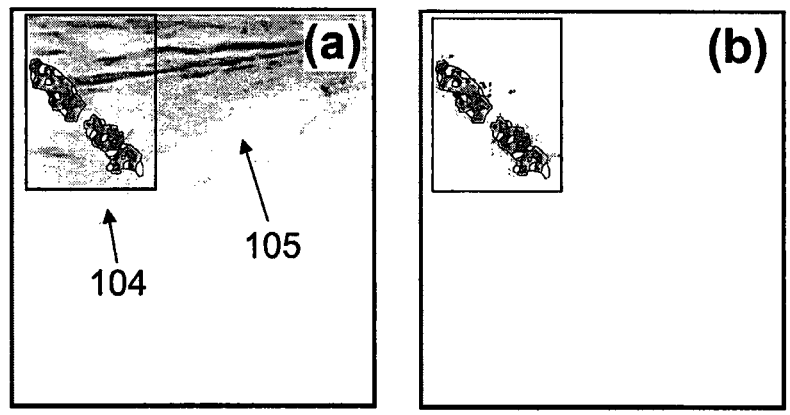
FIG. 3 shows received image data of a vibrating needle in a porcine test subject (a) before and (b) after data extraction.

At stage 200, Doppler ultrasound image data 104 is received together with B-mode ultrasound image data (indicated generally by numeral 105), as can be seen in FIG. 3(a). The Doppler ultrasound image data is in RGB format (i.e. pixels with independent values between 0-255 for each of three values for red, green and blue) and the B-mode image data is in greyscale format (i.e. pixels with a single intensity value of 0 to 255 for each of the three values). In alternative embodiments, the first image data comprises only Doppler ultrasound image data. B-mode ultrasound image data (which may be acquired simultaneously or sequentially) may be received separately at stage 202.

In order to reduce data processing demands, the data can be extracted, selected, and/or transformed.

FIG. 3(a) shows the received Doppler and B-mode image data of a vibrating needle in a porcine test subject. FIG. 3(b) shows Doppler image data after the extraction of all pixels not having the equal intensity value for each of the RGB values. Extraction of data in this way removes the greyscale data which might otherwise lead to errors in location determination.

In an alternative embodiment, all RGB data is transformed to greyscale format. Pixels with an intensity value above a threshold value may then be extracted. In other embodiments, data may be transformed using a compression algorithm.

Figure 4:
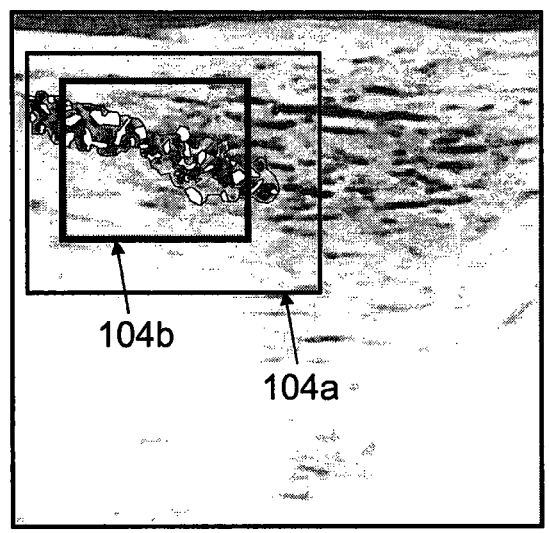
FIG. 4 illustrates data selection from received image data of a vibrating needle in a porcine test subject.

Optionally, a data region of interest 104a or 104b may also be selected—as illustrated in FIG. 4. Data selection can be conducted before or after extraction.

Figure 5:
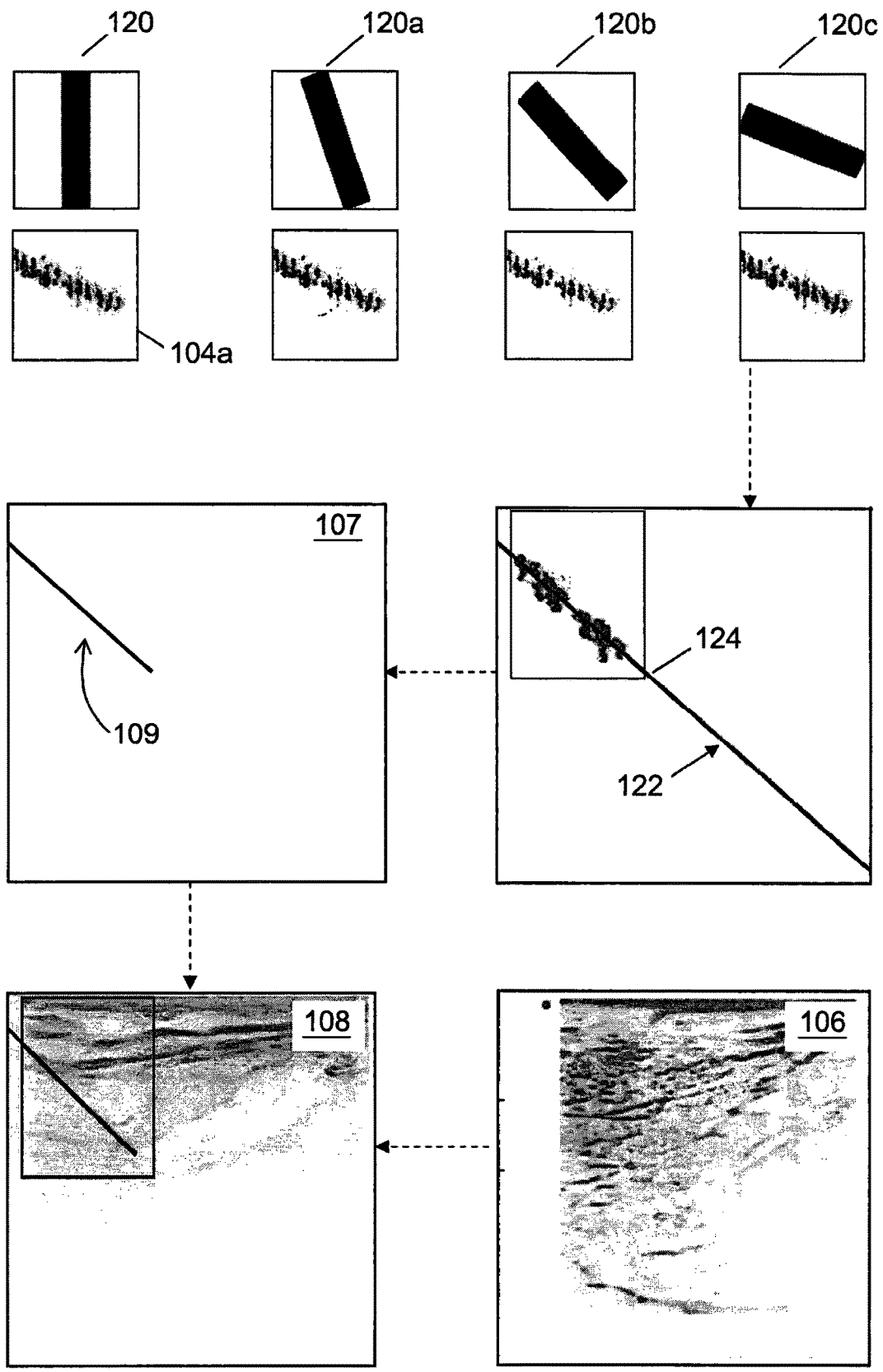
FIG. 5 illustrates fitting of extracted and selected first image data by matrix matching and end point determination, generation of a representation of a structure, and generation of a composite image from the representation and second image data.

Determining the location of the introduced needle 7, at stage 204, may include fitting the first image data to structural data representing the introduced needle. In the example illustrated in FIG. 5, the data is fit by matrix matching to determine an orientation of the needle. A mask 120 (structural data representing a straight reflective edge of the needle) is generated, consisting of a matrix with values 1 inside the mask (white) and 0 outside the mask (black) and subjected to a series of rotational transformations to produce masks 120a, 120b, 120c etc. Fitting is conducted by (i) determining a maximum correspondence (a value obtained by multiplying matrices and summing RGB values for all pixels) between the masks 120, 120a, b, c and the extracted and selected Doppler data 104a (ii) determining a best fit line 122 with a gradient corresponding to the orientation of the mask 120c having maximum correspondence with the data 104a (iii) determining an end point, corresponding to the distal end of the needle, by searching for the final pixel having a non-zero value along the best fit line 122. A calculated image 107 is generated, which includes a representation 109 of the needle. The calculated image may then be overlaid onto a second B-mode ultrasound image 106, to generate the composite image 108.

In alternative embodiments, the fitting may include a principal component analysis of extracted Doppler data, in order to obtain orientation information.

The composite image includes a representation 109 of the needle, and it has been shown that the location can more accurately be seen over B-mode images, than in conventional combined Doppler/B-mode ultrasound images. In addition, B-mode information in the proximity of the needle is not obscured by blurring and artefacts in the Doppler image.

The composite image may be updated (for example at the frame rate of a standard video format) so that a clinician may be provided with an animated representation of the needle plotted over a B-mode ultrasound video, to assist in ultrasound guided procedures.

It has also been found that the optimum amplitude and frequency of needle vibration is reduced in comparison to previously known methods, in order to generate Doppler ultrasound image data sufficient for accurate location determination and without the blurring and artefacts associated with existing methods and apparatus, as described in further detail below.

Figure 6:
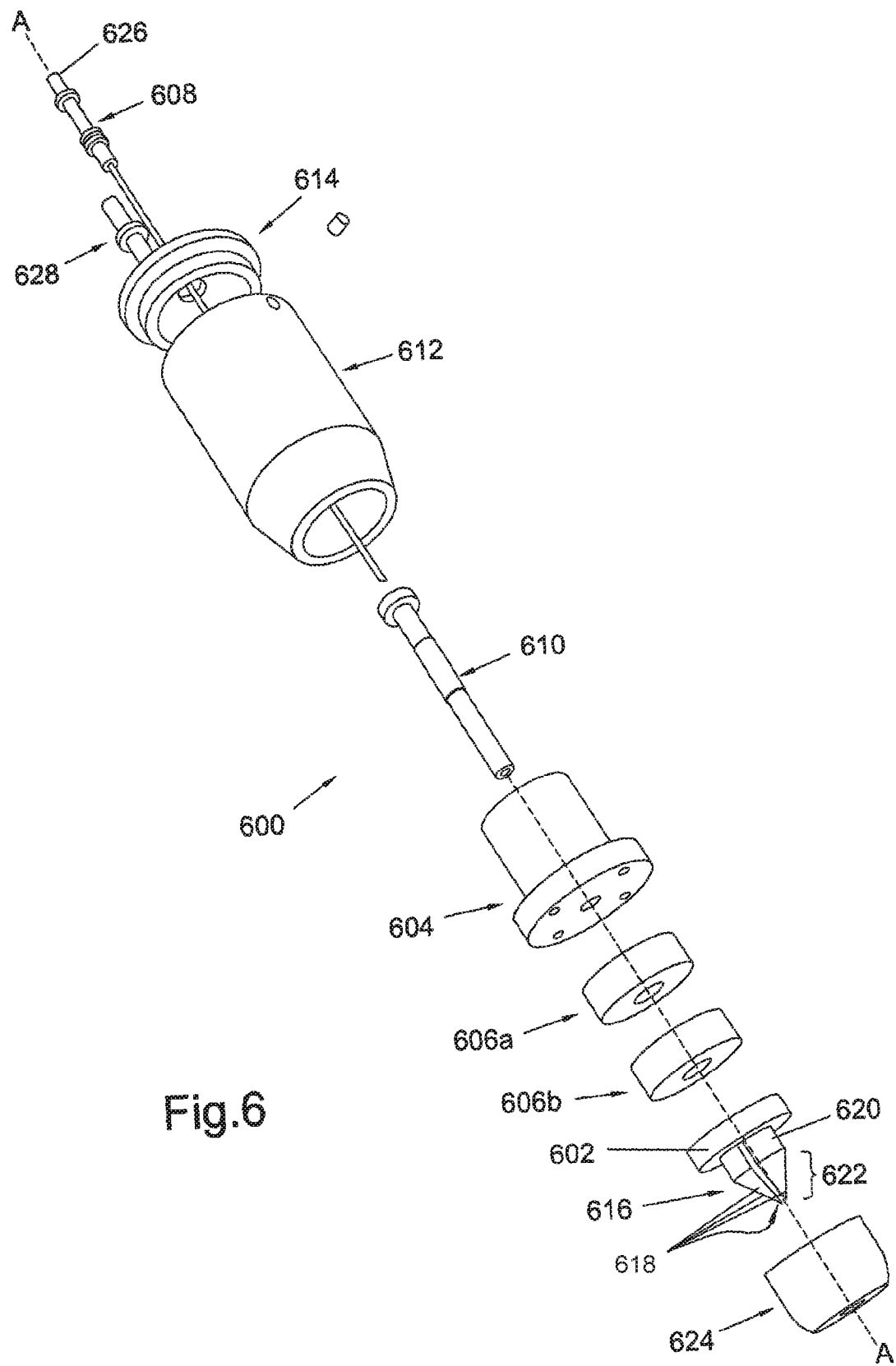
FIG. 6 is an exploded view of an ultrasonically actuated medical implement.

An exploded view of an ultrasonically actuated medical implement 600 of the present invention is shown in FIG. 6. The medical implement has a first mass assembly 602 and a second mass assembly 604. A channel extends along a principal axis A and is defined at in part by the mass assemblies. A piezoelectric element 606a, 606b is operable to cause reciprocation between the first and second mass assemblies along the principal axis. A probe member (a standard hypodermic needle) 608 may be received in the channel and fixedly coupled to the first mass assembly.

The piezoelectric element is of the Langevin type and comprises a stack of lead zirconate titinate ceramic rings. The rings are held between the first and second mass assemblies by hollow pre-stress bolt 610 which extends through a bore running through the mass assemblies and the piezoelectric element.

The mass assemblies are housed within a body (consisting of casing 612 and casing cap 614) and the position of the second mass is fixed in relation to the pre-stress bolt and the body.

Electrical connection with the piezoelectric element may be established via connector 628. As described in further detail below, actuation of the piezoelectric element (by application of a suitable voltage), causes the relative positions of the mass assemblies along the principal axis to change and thus for the first mass assembly to reciprocate along the principal axis in relation to the second mass assembly and the body.

The mass of the second mass assembly is much larger than that of the first mass assembly (10:1 ratio), ensuring that the combined mass of the second mass assembly and the body is greater than the combined mass of the first mass assembly and the needle. This ensures efficient transfer of ultrasonic energy to the needle, in use.

The body is generally cylindrical and sized to be gripped in the manner of a pen, for ease of manual manipulation in use.

A distal portion of the first mass assembly includes a connection arrangement 616 for fixing the needle to the first mass assembly. The connection arrangement consists of four engagement members 618 having an externally threaded portion 620 and a tapered portion 622. A collet nut 624 has corresponding internal threaded and tapered portions (not shown) and is threadable around the engagement members to apply a radially inward force to the engagement members. Thus, by tightening the collet nut, the engagement members can be forced into engagement with the needle.

The connection arrangement thereby applies even pressure around a length of the needle and the engagement members have sufficient range of motion to accommodate a range of needle diameters. In addition, the needle can be coupled to the first mass assembly very quickly and easily. Once the collet nut is threaded far enough to bring the respective tapered portions into initial contact, sufficient clamping force can be applied to the needle by tuning the collet nut a further quarter of a turn, which can be accomplished in a single manual operation, without the need to grip and re-grip the nut.

The bore extends all the way through the body, from the distal end of the connection arrangement, through the pre-stress bolt (and thus the mass assemblies and piezoelectric element) and through the casing cap. The body is sized so that a standard needle extends beyond each end of the body. This enables connection of the proximal end 626 of the needle directly to a fluid source or other medical apparatus. In contrast to apparatus where a needle is attached to one end of a medical implement, connection need be established directly with the proximal end of the body, which reduces risk of contamination.

In alternative embodiments (not shown), other piezoelectric materials are employed and/or the piezoelectric element has an alternative configuration. For example, the piezoelectric element may include Mn-doped single crystal transducers, which may be configured as plates or rods to either side or around the bore.

In one embodiment, the piezoelectric element includes a piezoelectric motor configured to apply a rotational force between the first and second mass elements around the principal axis, to further reduce accretion to the needle and required penetration forces, in use.

Figure 7:
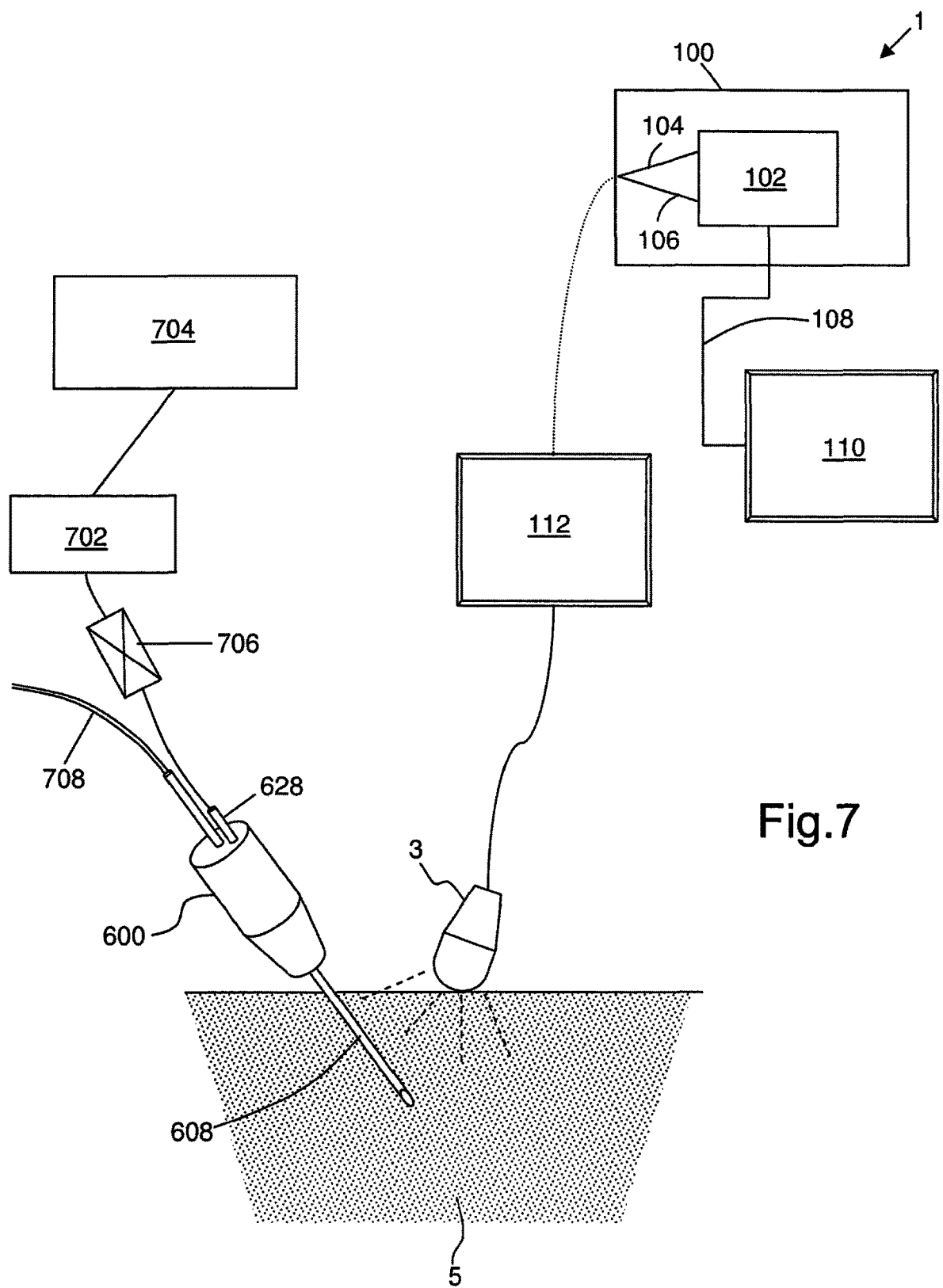
FIG. 7 is a schematic diagram of an actuation system for conducting percutaneous procedures using the medical implement shown in FIG. 6 and a medical imaging system.

FIG. 7 shows an actuation system 700 for conducting percutaneous procedures using the medical implement 600. The system includes a power amplifier 702 and waveform generator 704. These are connected to terminal 628 on the medical implement. The power amplifier and signal generator are together operable to apply a drive voltage to the piezoelectric element at with a frequency range of 10-100 kHz, thus causing the needle to reciprocate at a selected ultrasonic frequency. The actuation system also includes an impedance matching circuit 706. In alternative embodiments (not shown) the matching circuit is housed in the body.

The drive circuitry (comprising the amplifier, signal generator and matching circuit) may be manually adjusted to tune the resonance frequency of the piezoelectric circuit, such that the device can be optimized for different types of needle or different target regions. In the embodiment shown, the signal generator is manually adjustable.

In the embodiment shown, the system is configured to cause the needle reciprocate along the principal axis with a resonant frequency of 21 kHz and an amplitude (i.e. peak to peak range of motion) in the range of 0 to 100 µm, depending on the applied drive voltage. A drive voltage (peak to peak) in the range of 0-100 V is required in order to induce motion of this amplitude in the Langevin piezoelectric element 606a,b. Optimal needle visibility has been observed at 20V and below.

Ultrasound guided medical procedures are commonly used in clinical practice. However, whilst ultrasound images may show useful information concerning anatomical structure, it can be difficult in practice to observe the location of the medical implement. Echogenic needles (having a regular array of surface deformations) improve visibility to some degree and some clinicians also use Doppler mode imaging during procedures to help to locate needles. However, echogenic needles have shown limited benefits, they are expensive and manipulation of needle in tissue (during procedure) can be very painful.

Needles can be manually moved to generate a Doppler signal, or fluid can be injected to help to locate the tip of a needle. However, additional movement or injection may not always be possible and a Doppler image may not in any case show the location of a needle precisely. "Colormark" (a trademark of NuVue Therapeutics, Inc) biopsy needles are also known which include a needle driven by a piezoelectric circuit to generate a strong Doppler ultrasound image. However the radial motion of the needle which is induced generates a blurred Doppler signal and the apparatus cannot be used in procedures where precise needle positioning is critical (e.g. when injecting into nerves).

The ultrasound actuated medical implement 600 has been shown to provide for improved visibility both in conventional ultrasound imaging techniques, using ultrasound probe 3 with a conventional ultrasound imaging system and with imaging system 1.

Tests of the ultrasound actuated medical device 600 and system 700 have been conducted using a conventional ultrasound imaging system 112—an SonixTablet ultrasound imaging system (SonixTablet is a trade mark of Ultrasonix Medical Corporation, Richmond, BC, Canada)—and a standard 5 MHz ultrasonic imaging probe 3. Needle visibility tests of the needle of implement 600 introduced into a range specimens were conducted using conventional B-mode and Doppler imaging modes have been conducted. Needle visibility tests were also conducted in which image data output from imaging system 112 was received and further processed by imaging system 1—in the form of an image processing algorithm running on Matlab (published by Mathworks Inc., Cambridge, UK) on a standard PC. The apparatus used for these tests is schematically illustrated in FIG. 7.

Specimens:

A variety of specimens were used in stages as the study on the effects of various factors on the performance of the needle actuation device continued. This allowed assessment of the device's performance in different conditions i.e. in or mimicking different tissues.

Initial studies were conducted using an agar-based tissue-mimicking "phantom" material was used. Phantom has acoustic properties which are similar to human tissues (Bude and Alder, 1995). The phantom was prepared following the method described by Zell et al., 2007. and was used within 24 hours of preparation.

Studies were also conducted using ex-vivo Ox liver and porcine tissue and subsequently tests were conducted using soft embalmed cadavers preserved by the Thiel method. Tissues of Thiel embalmed cadavers are accepted as providing a realistic substitute for living tissues for teaching and research in various procedures including orthopaedic surgery, laparoscopy, endoscopy and image guidance interventional procedures (McLeod et al., 2010).

Protocol:

Studies were conducted using the in-plane imaging technique, in which the needle was introduced into the target region of the specimen generally in the plane of the ultrasound transceiver array of the probe 3. This is the most common ultrasound technique in clinical use because it provides visibility of needle shaft and trajectory (Corner and Grant, 2012).

Needle Penetration Force Test

Tests of the force required to penetrate a variety of specimens were also conducted, using a load testing machine (H5KS, Tinius Olsen Inc., Horsham, USA) adapted to measure forces required to maintain a controlled motion at a constant speed through the specimen.

The effects of needle actuation drive voltage, frequency and insertion speed (in the range of 300-500 mm/min) were investigated.

Needle Visualization Tests

B-Mode

Figure 8:
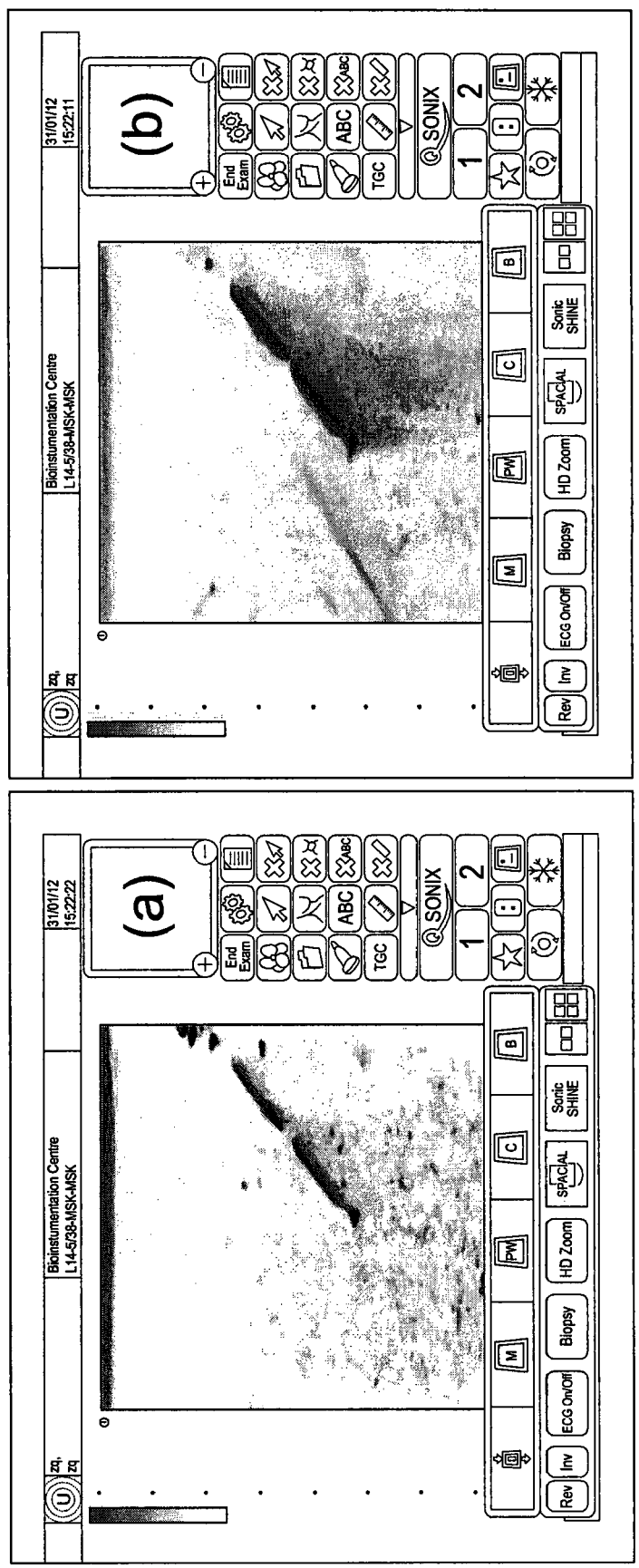
FIG. 8 shows a B-mode ultrasound image of (a) a stationary (b) an ultrasound actuated echogenic needle in phantom.

FIG. 8 shows two images of an echogenic needle introduced into phantom. FIG. 8(*a*) shows an image of a stationary needle (i.e. where the actuation apparatus 702, 704, 706 is switched off and FIG. 8(*b*) shows the ultrasound activated needle (b). Although the needle was clearly visible even when stationary, actuating the needle further enhanced its visibility by delineating it as a bright white line compared to the pale grey line, observed without actuation.

Doppler Mode

Figure 9:
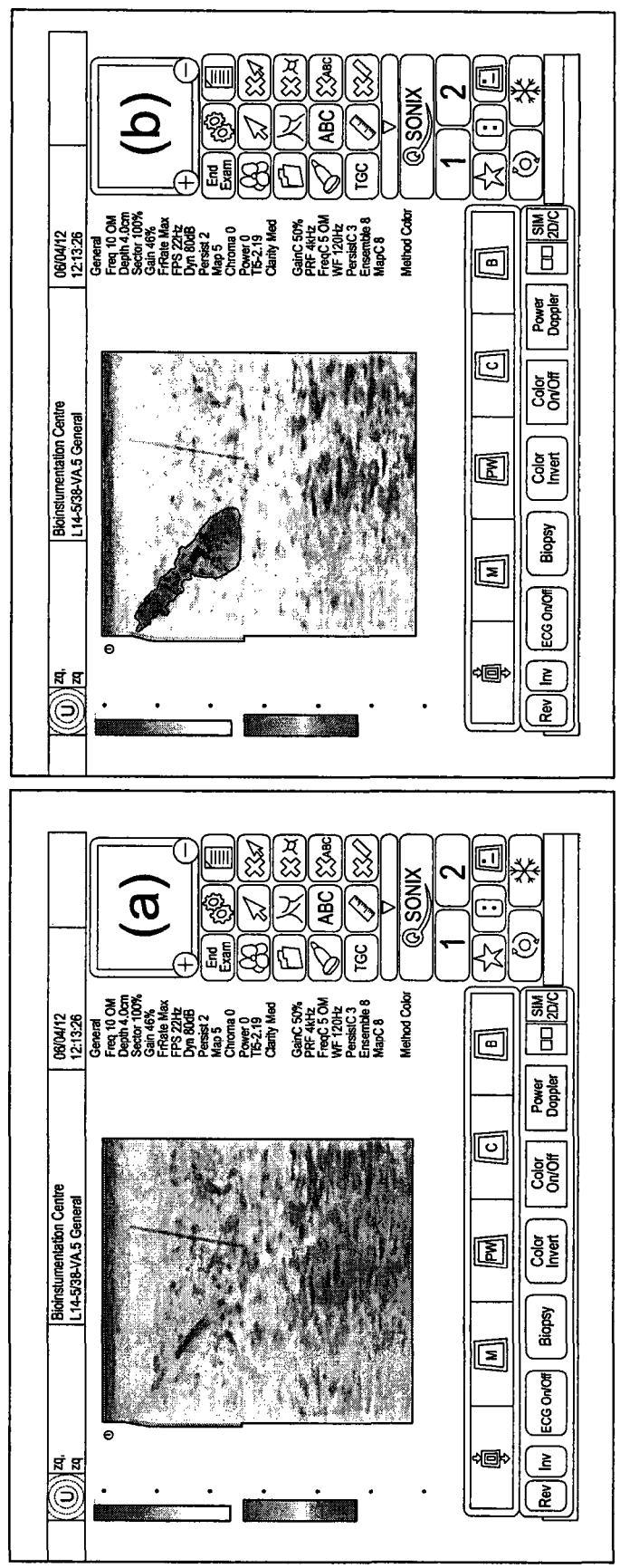
FIG. 9 shows a colour Doppler mode ultrasound image of (a) a stationary (b) an ultrasound actuated echogenic needle in phantom.
Figure 10:
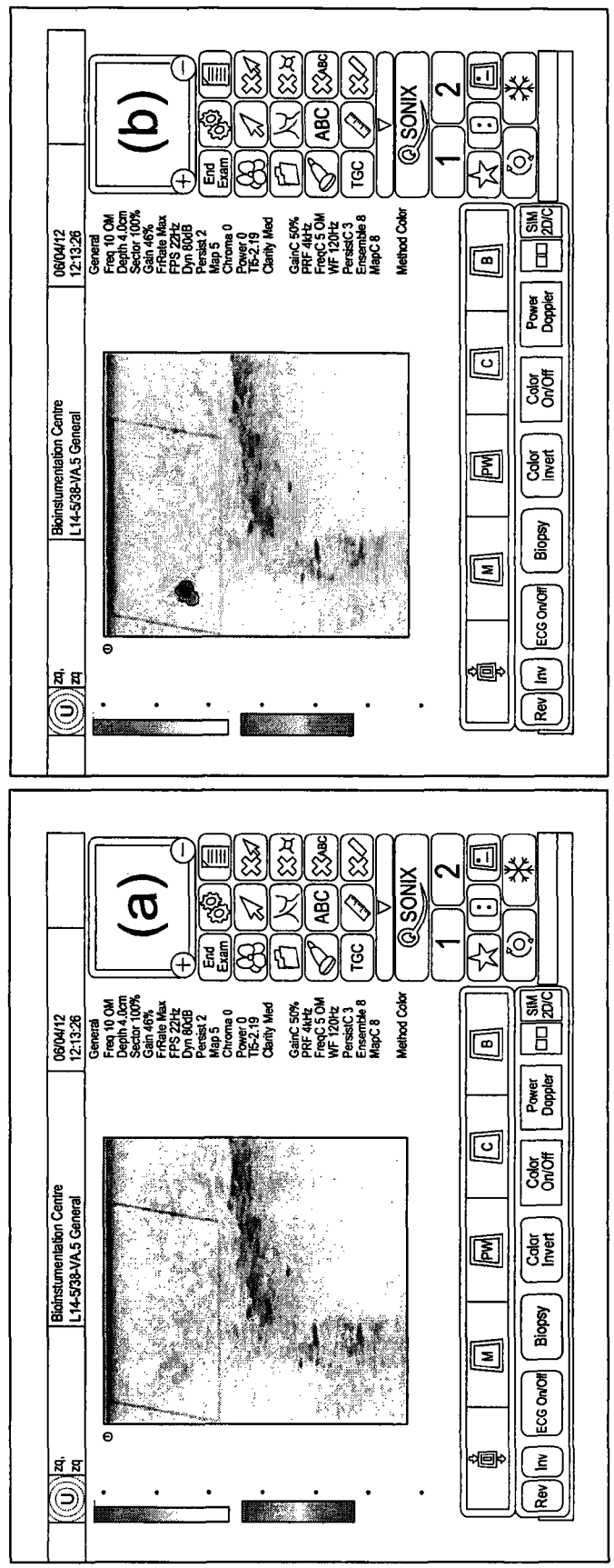
FIG. 10 shows a colour Doppler mode ultrasound image of (a) a stationary (b) an ultrasound actuated standard needle in phantom.

The effectiveness of activated needles was also observed using colour Doppler imaging mode. FIGS. 9 and 10 show the images captured for, respectively, an echogenic and a standard needle using colour Doppler mode.

These results show that actuation combined with colour Doppler further enhances the visibility of the echogenic needle by revealing the whole shaft of the needle. The tip of the standard needle was also visible.

Ex-Vivo Tissues

Figure 11:
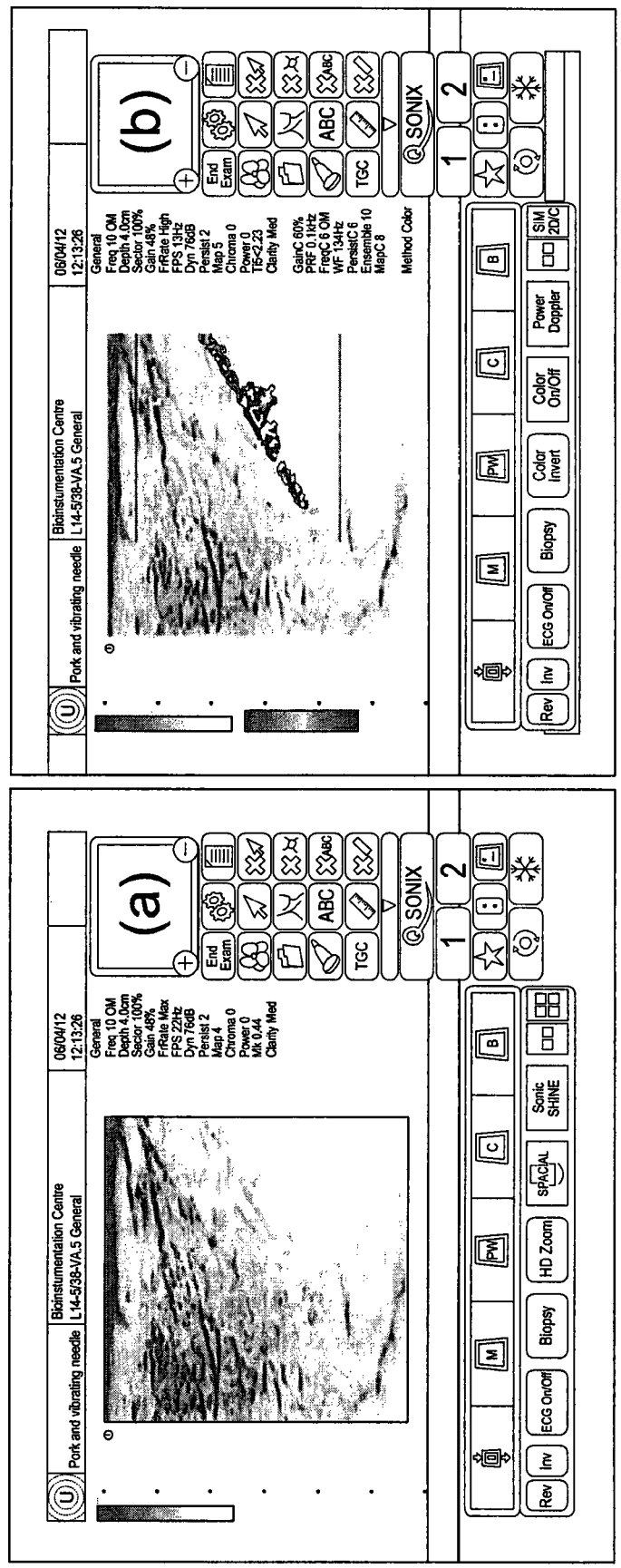
FIG. 11 shows a colour Doppler mode ultrasound image of (a) a stationary (b) an ultrasound actuated echogenic needle in porcine tissue.

FIG. 11 shows an echogenic needle in porcine tissue (a) stationary and (b) ultrasonically actuated. Actuation can clearly be seen improve delineation of the echogenic needle in porcine tissue. In contrast, the needle and its tip are barely visible when the needle is stationary.

Figure 12:
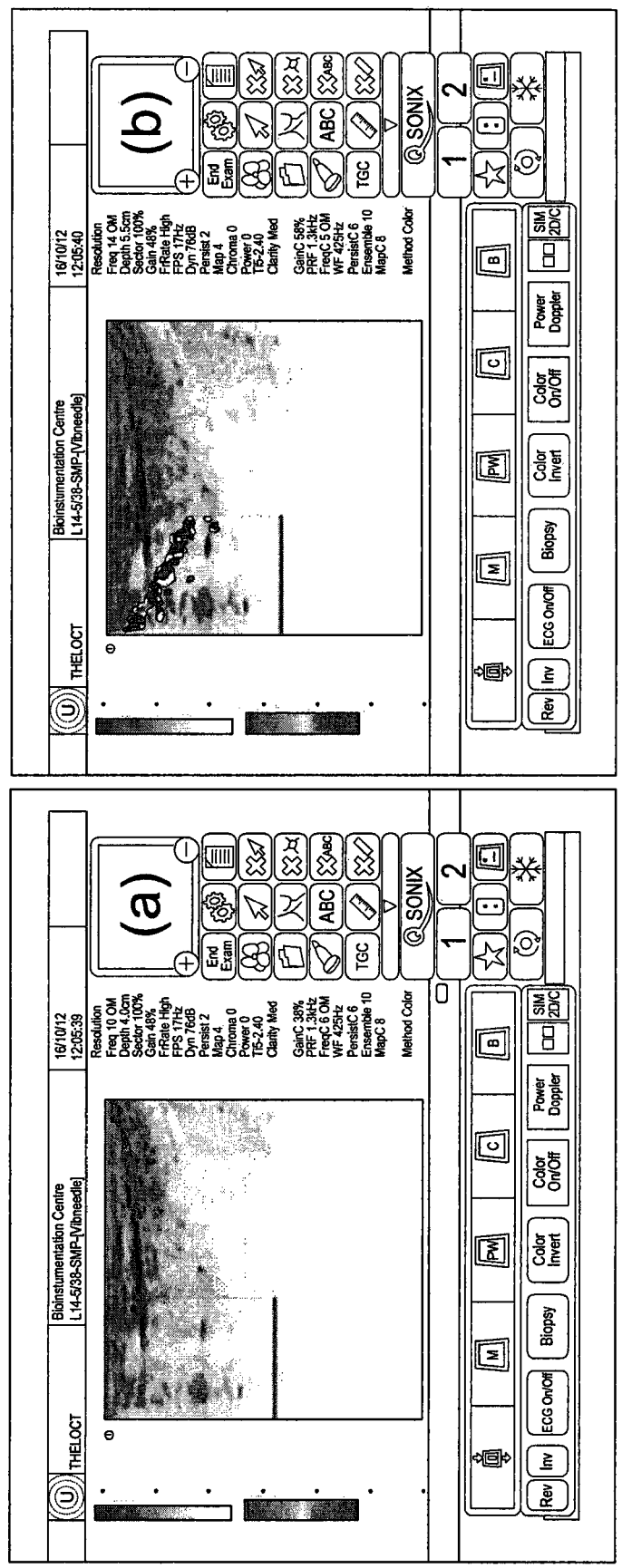
FIG. 12 shows a colour Doppler mode ultrasound image of (a) a stationary (b) an ultrasound actuated standard needle in the lower abdomen region of a Thiel embalmed cadaver.
Figure 13:
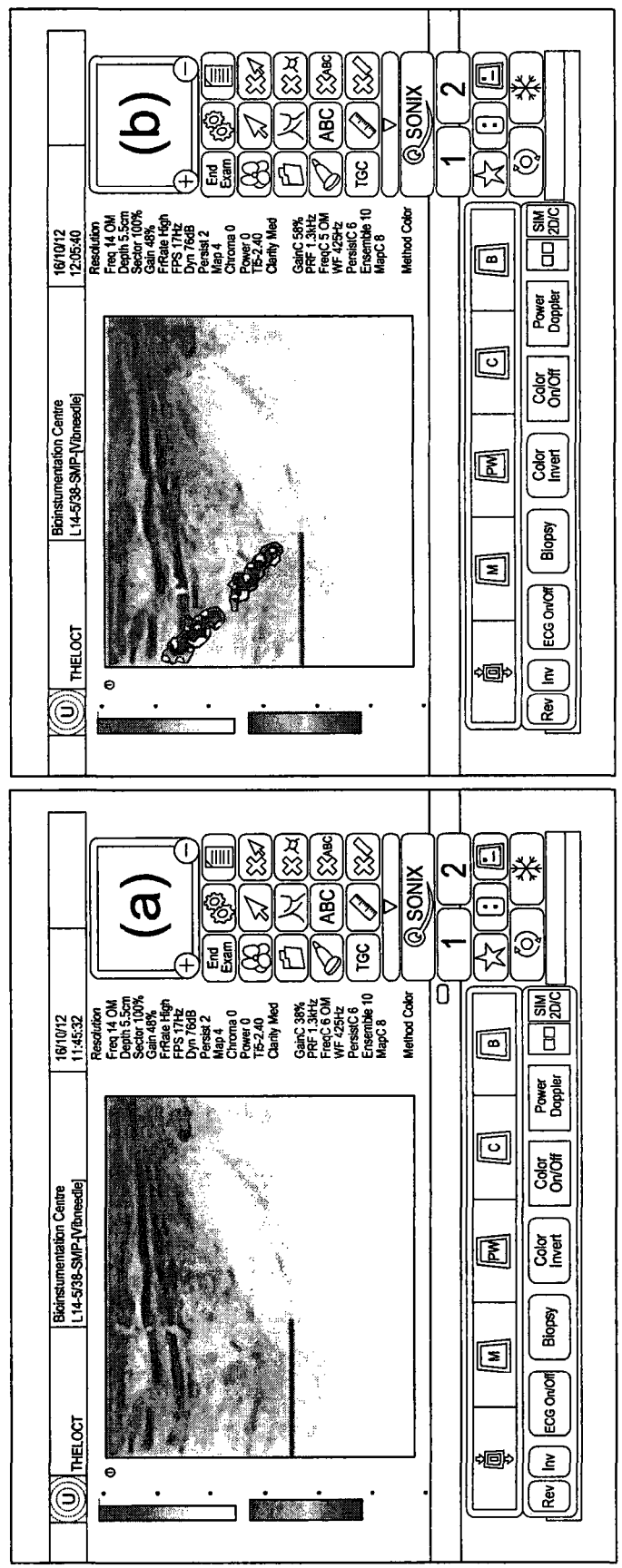
FIG. 13 shows a colour Doppler mode ultrasound image of (a) a stationary (b) an ultrasound actuated echogenic needle in the lower abdomen region of a Thiel embalmed cadaver.

FIGS. 12 and 13 show the effect of activation on visualization of standard and echogenic needles respectively, introduced into the lower abdomen region of a Thiel embalmed cadaver.

Figure 14:
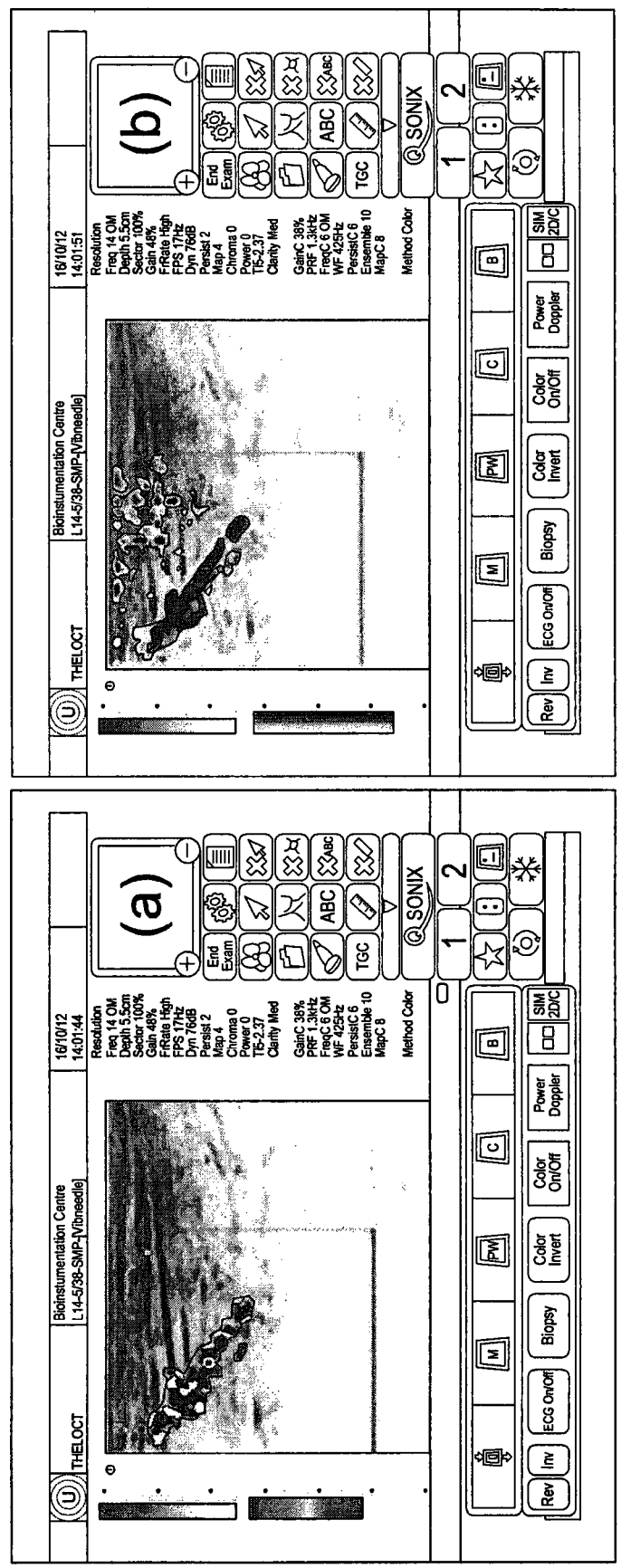
FIG. 14 shows (a) a colour Doppler mode ultrasound image (b) a power Doppler mode ultrasound image of an ultrasound actuated echogenic needle in the lower abdomen region of a Thiel embalmed cadaver.

FIG. 14 shows images of the standard ultrasound actuated needle in (a) colour Doppler mode and (b) power Doppler mode.

Drive Voltage Variation

Figure 15:
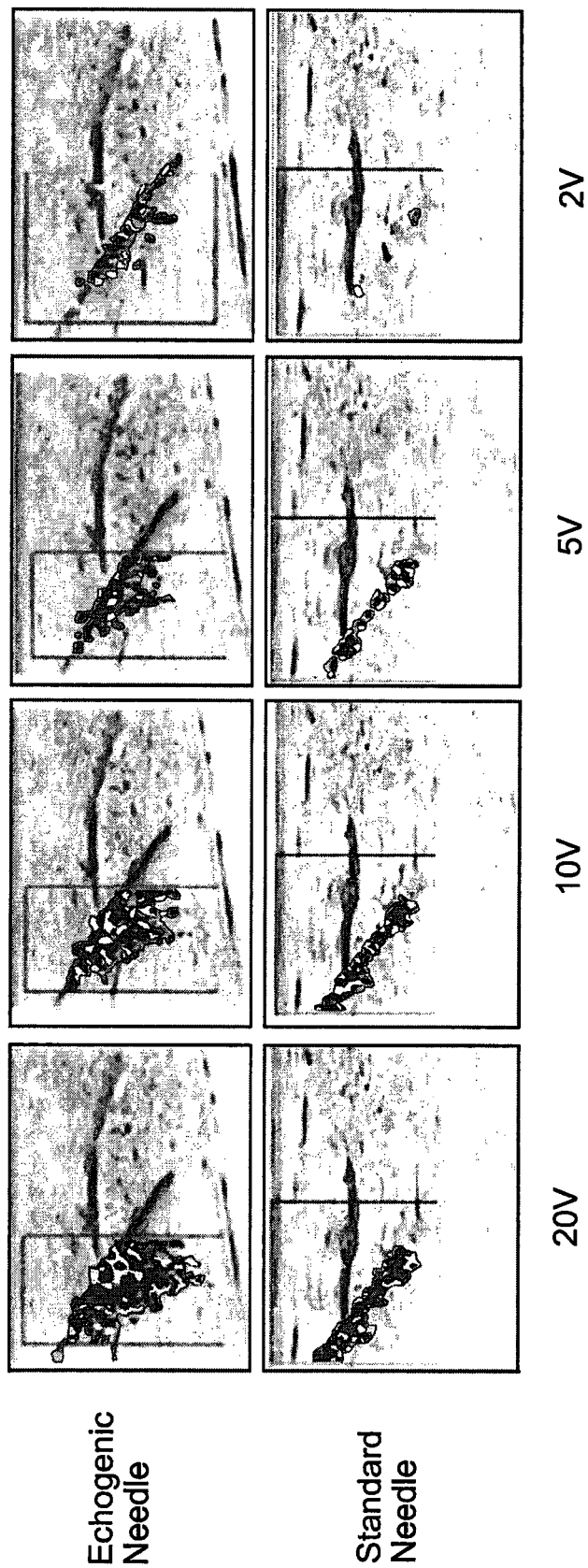
FIG. 15 shows images of an echogenic and a standard ultrasound actuated needle in an Ox liver specimen at drive voltages of 20V, 10V, 5V and 2V.

FIG. 15 compares the visibility of both standard and echogenic needles in an Ox liver specimen as a function of drive voltage. The drive voltage was incremented from 2V to 20V at the resonant frequency of the device, 21.6 kHz. These drive voltages correspond to motion amplitudes in the range from approximately upto 50 μm.

Images of the echogenic needle show more noise and artefacts, especially below the needle, than images of the standard needle. The intensity of the noise and artefacts is greater with increase drive voltage, and thus a greater amplitude of needle oscillation.

For the echogenic needle, visibility was optimized at 2V (corresponding to amplitude of around 5 μm). At this voltage, the needle can be identified and noise is minimal. Although the intensity of the Doppler signal is larger at higher voltages, the strong artefact below the needle makes it difficult to identify the location needle shaft and tip accurately.

The effects were less pronounced in the images of the standard needle and visibility was optimized at a slightly higher voltage of 5-10V (the optimal amplitude being estimated at around 10 μm). However, even at 2V, identification of tip of the standard needle is possible.

For both types of needle, visibility was optimal for much lower amplitudes of motion than that associated with, for example, ultrasound actuated drills or needles which are adapted specifically to reduce required penetration force (which typically oscillate with amplitudes of more than 100 μm).

It was also observed that the resonant frequency of the device changed due to the loading conditions during needle insertion. Performance was optimized by manual adjustment of driving frequency to match the resonant frequency of the device.

Needle to Beam Angle

Figure 16:
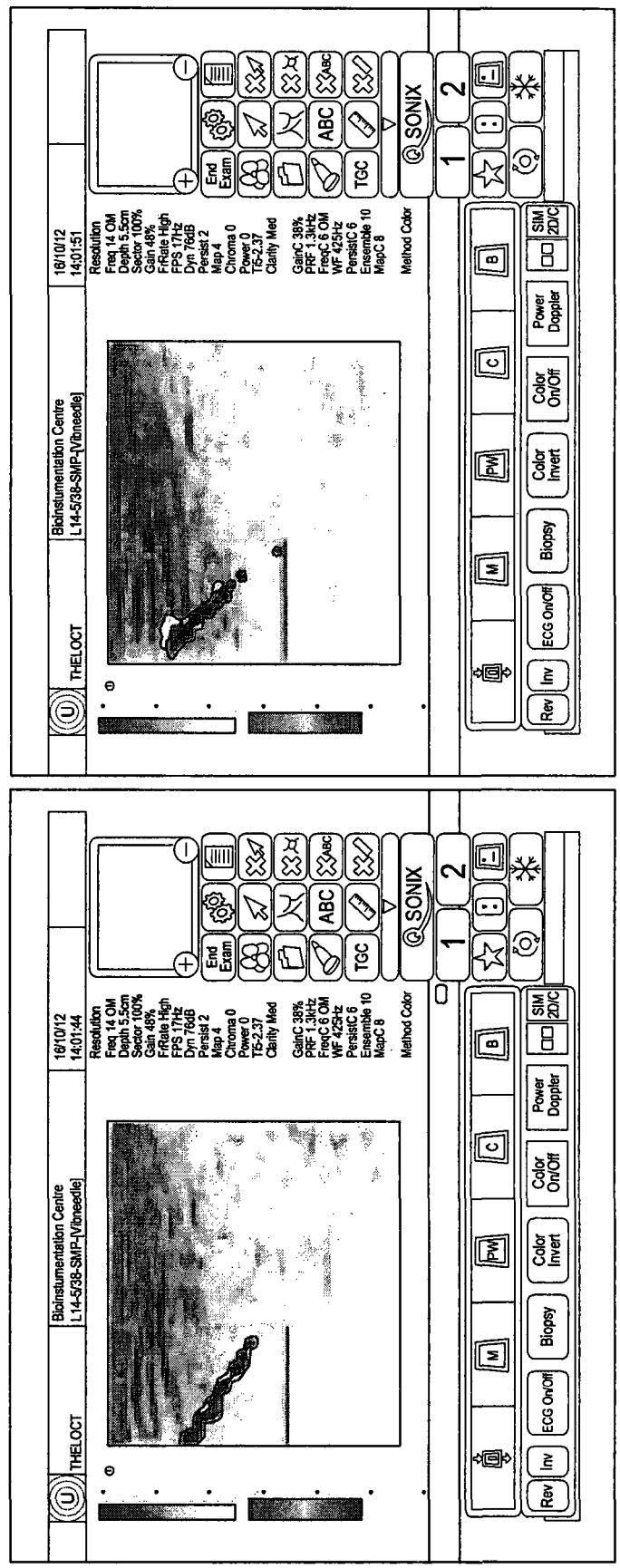
FIG. 16 shows a colour Doppler mode ultrasound images of an ultrasound actuated standard needle in the lower abdomen region of a Thiel embalmed cadaver at insertion angles of (a) 30°, (c) 45° and (d) 55° in relation to an ultrasound probe held in a fixed position perpendicular to the outer surface of the specimen.
Figure 16:
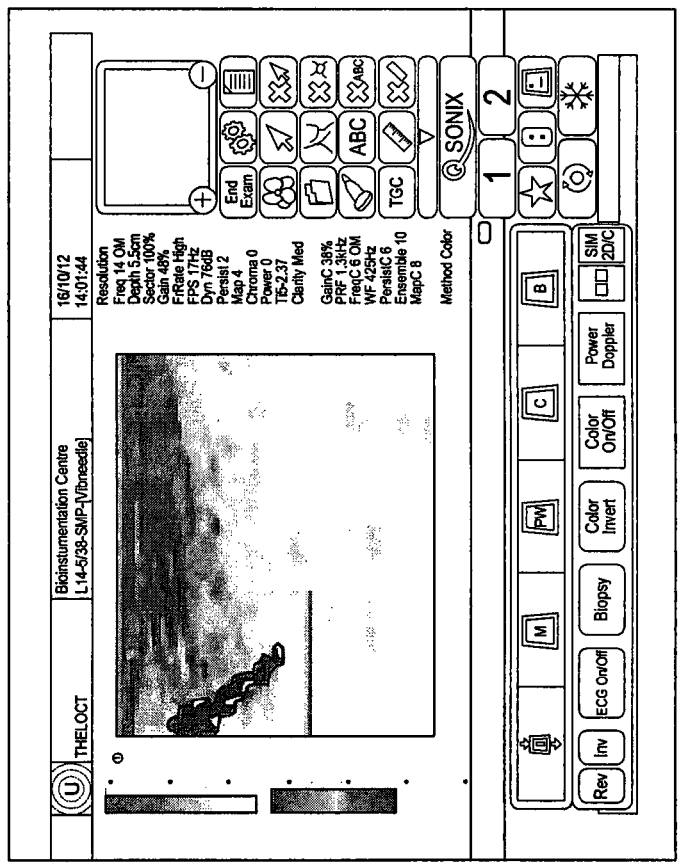

FIG. 16 shows the effect of three needle insertion angles (approximated) of (a 30°), (c) 45° and (d) 55° in relation to a fixed position of the ultrasound probe, using an actuation voltage of 10V.

Penetration Force Test

Ultrasound guided procedures can be compromised by poor needle visualisation (Carr et al., 2001) and/or needle deflection (Roberson et al., 1997)—potentially resulting in target misplacement.

Needle deflection is proportional to the penetration force, and also depends on bevel tip and diameter of the needle (Kataoka et al., 2002; Okamora, Simone and O'Leary, 2004). The properties of the tissue into which the needle is inserted also contributes to needle deflection.

Figure 17:
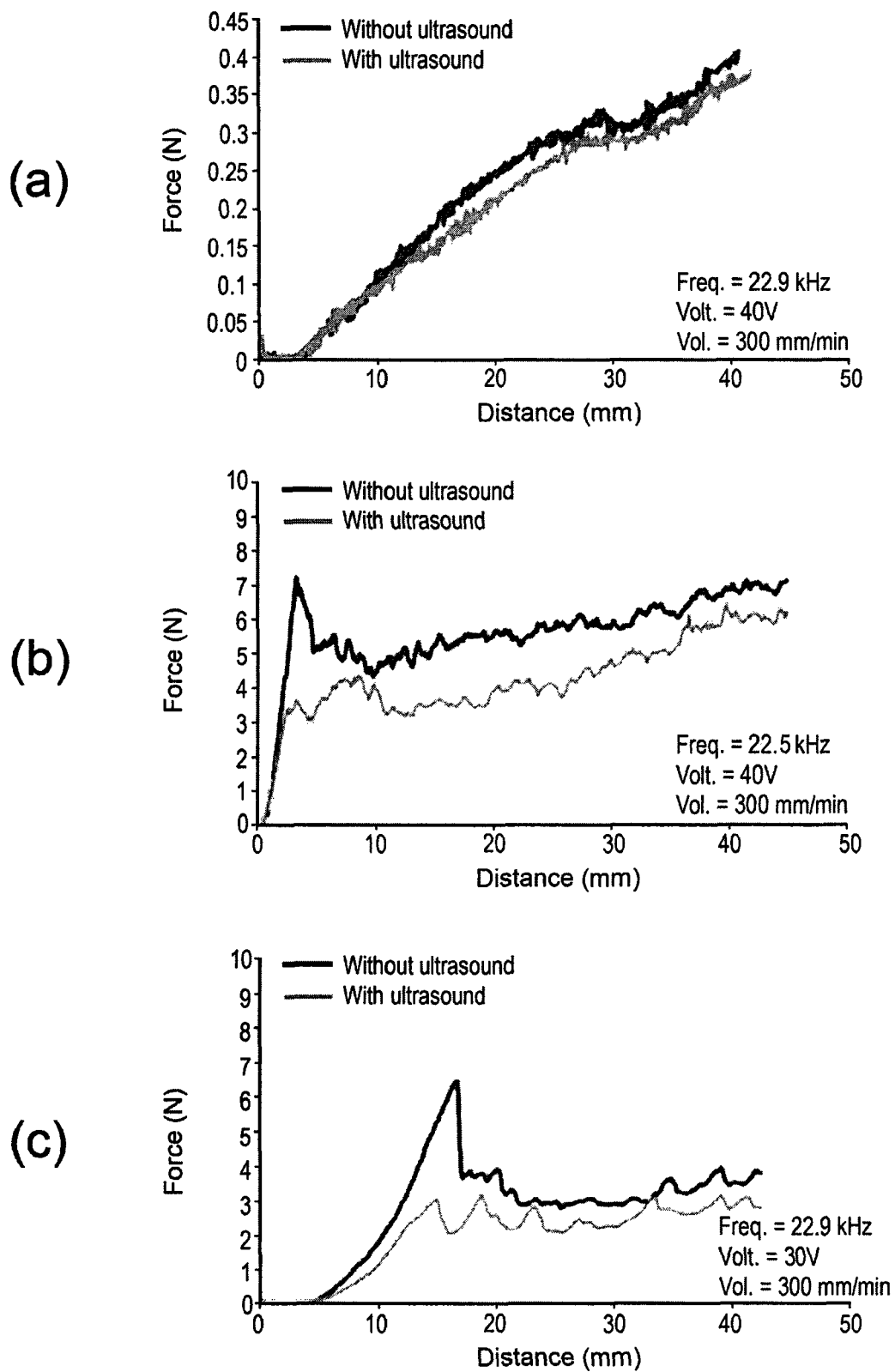
FIG. 17 penetration force required to penetrate (a) phantom (b) sawbone and (c) porcine tissue using a stationary and an ultrasound actuated standard needle.

Tests were conducted to study the effect of needle actuation on the force required to penetrate a needle into a variety of specimens. FIG. 17 shows test results of the penetration force required to penetrate (a) phantom (b) sawbone and (c) porcine tissue, and the effect of needle actuation on the force response.

The upper plot in each case corresponds to a non-actuated needle, indicating that ultrasound actuation reduces the required penetration force. In case of sawbone and porcine tissue samples, ultrasound actuation resulted in a 28.9% and 38% reduction in force required for initial tissue penetration.

Image Processing

Figure 18:
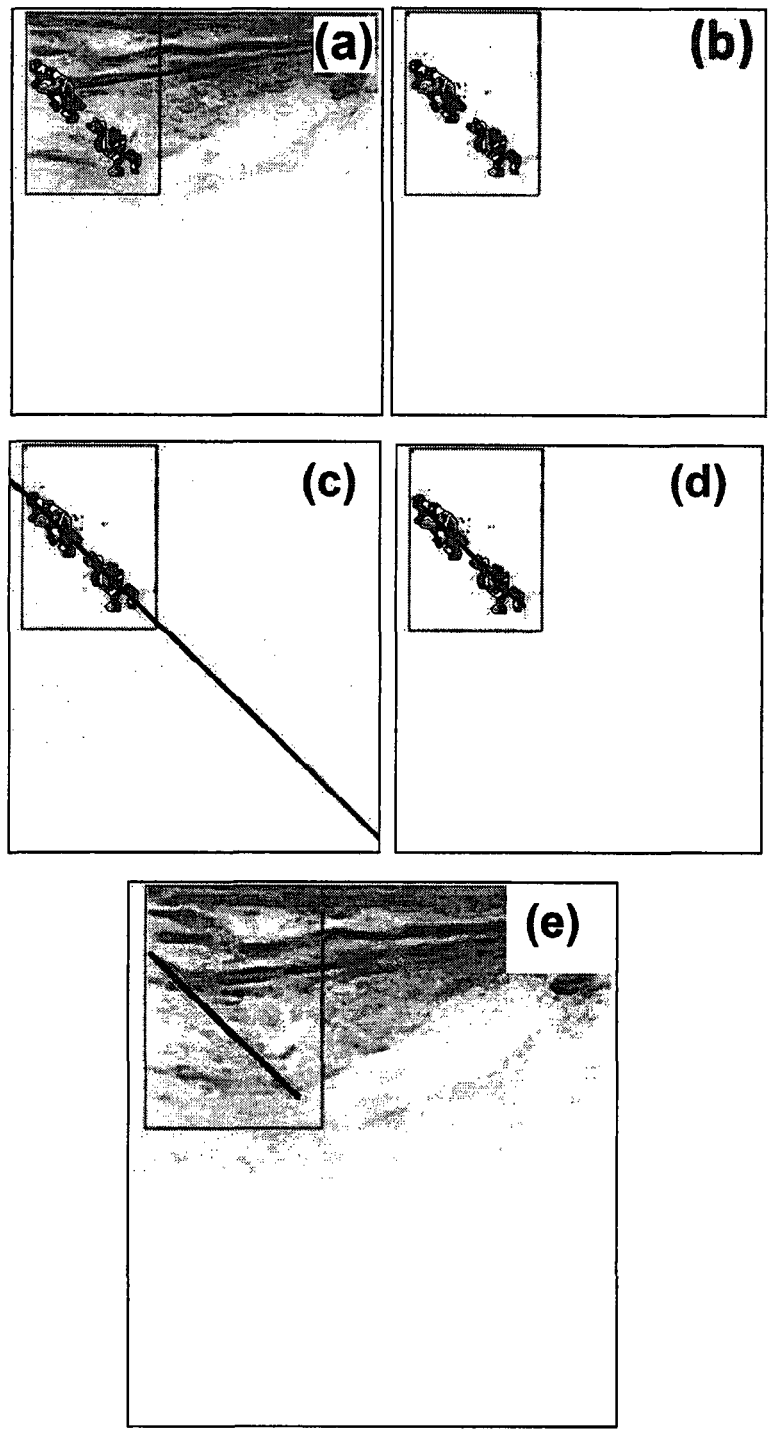
FIG. 18(a)-(e) illustrates the image processing steps conducted in order to generate a composite image of an echogenic needle in the lower abdomen region of a Thiel embalmed cadaver.

The image processing methods described above were also applied in order to improve needle visibility, as shown in FIG. 18.

FIG. 18(a) shows a combined colour Doppler and B-mode ultrasound image of porcine tissue, output by the SonixTablet. FIG. 18(b) shows an extracted image in which all pixels having non-equal RGB values have been extracted, thereby separating pixels representing the Doppler ultrasound image from the greyscale B-mode image, and "flattening" the background. FIG. 18(c) shows a best fit line indicative of the slope of the needle (calculated by the matrix matching method described above), plotted on to the extracted image. FIG. 18(d) shows the line plotted onto the extracted image, following determination of the end point of the needle. The plotted line is a representation of the orientation and position of the tip of the needle. FIG. 18(e) shows a composite image of a B-mode ultrasound image (obtained very shortly after the image of FIG. 18(a) on the same target region) with the plotted line representation of FIG. 18(d) overlaid.

The composite image improves needle visualisation because the needle representation obscures a minimal part of the B-mode image and the location and orientation of the needle can be more precisely observed than from noisy Doppler ultrasound images.

DISCUSSION AND CONCLUSION

It has been shown that ultrasonically activated needles coupled with colour Doppler imaging modality have great potential in a range of percutaneous procedures. It allows the clinicians to visualise the whole shaft and the tip of standard medical needles. Activated echogenic needles are more visible than the activated standard needles and visualisation is optimal at lower drive voltages than comparable standard needles.

In order to reduce the noise associated with Doppler's mode and to better delineate the needle and its tip with high accuracy on grey scale image, a method of generation of a composite image including a calculated representation of the needle an image processing algorithm has been developed. The processing time required to process and update an image is under 10 seconds and can be achieve in real time using a more powerful processor and optimisation when integrated into an imaging system.

It has also been shown that the needle actuation is effective in reducing the penetration force and thus needle deflection when the needle in inserted into a tissue, despite comparatively low drive voltages and amplitude of needle motion used.

The invention claimed is:

1. An ultrasonically actuated medical implement, comprising:
   a first mass assembly and a second mass assembly;
   a channel extending along a principal axis and defined at least in part by the mass assemblies;
   a probe member received in the channel and fixedly coupled to the first mass assembly; and
   a piezoelectric element operable to cause reciprocation of the first mass assembly and the probe member in relation to the second mass assembly along the principal axis;
   wherein the first mass assembly and the second mass assembly are separate components; and
   wherein a mass of the first mass assembly is smaller than a mass of the second mass assembly and a ratio between the mass of the first mass assembly and the mass of the second mass assembly is in a range of 1:5-20.

2. A medical implement according to claim 1, wherein the medical implement is configured for use in percutaneous procedures.

3. A medical implement according to claim 1, comprising a body, wherein:
   the body comprises the first and second mass assemblies and the piezoelectric element, and the channel extends along a length of the body; and the probe member extends from the body at each end of the channel.

4. A medical implement according to claim 1, comprising a chuck for coupling the probe member to the first mass assembly.

5. A medical implement according to claim 4, wherein the chuck comprises engagement members, moveable into engagement with the probe member, to thereby couple the probe member to the first mass assembly.

6. A medical implement according to claim 5, wherein the engagement members are moveable radially into engagement with the probe member.

7. A medical implement according to claim 4, wherein the chuck is configured to couple the probe member to the first mass assembly by way of a single manual operation.

8. A medical implement according to claim 4, wherein the chuck comprises a locking member, moveable in relation to engagement members, to bring the engagement members into engagement with the probe member.

9. A medical implement according to claim 8, wherein the locking member is rotatable in relation to the engagement members.

10. A medical implement according to claim 9, wherein the locking member or the engagement members may be gripped and turned through a part of a turn so as to couple the probe member to the first mass assembly, in a single manual operation.

11. A medical implement according to claim 8, wherein motion of the engagement members in relation to the locking member is indexed.

12. A medical implement according to claim 4, wherein the chuck comprises a collet.

13. A medical implement according to claim 1, wherein the piezoelectric element is configured to be adjustable in terms of delivering an amplitude of the reciprocation.

14. A medical implement according to claim 13, wherein the amplitude is:
   mechanically limited; or
   limited by a maximum deflection of the piezoelectric element; or limited by a drive voltage applied to the piezoelectric element.

15. A medical implement according to claim 1, wherein actuation of the medical implement causes the first and second mass assemblies to reciprocate longitudinally along and around the principal axis.

16. A medical implement according to claim 1, wherein the piezoelectric element is disposed between the first mass assembly and the second mass assembly.

17. The medical implant according to claim 1, wherein the piezoelectric element is further operable to cause rotational motion of the first mass assembly relative to the second mass assembly.

18. A body of a medical implement, the body comprising:
- a first mass assembly and a second mass assembly;
- a channel extending along a principal axis and defined at least in part by the first and second mass assemblies;
- a piezoelectric element operable to cause reciprocation of the first mass assembly in relation to the second mass assembly along the principal axis; and
- a chuck for releasably and fixedly coupling the first mass assembly to a probe member, wherein, when fixedly coupled to the first mass assembly, the probe member is received in the channel;
- wherein the first mass assembly and the second mass assembly are separate components; and
- wherein a mass of the first mass assembly is smaller than a mass of the second mass assembly and a ratio between the mass of the first mass assembly and the mass of the second mass assembly is in a range of 1:5-20.

* * * * *